(12) United States Patent
Ikeda et al.

(10) Patent No.: US 8,404,621 B2
(45) Date of Patent: Mar. 26, 2013

(54) METHOD FOR IMMOBILIZATION, PHYSIOLOGICALLY ACTIVE SUBSTANCE-IMMOBILIZED CARRIER, CARRIER FOR IMMOBILIZATION, CARRIER, AND PROCESS FOR PRODUCING CARRIER

(75) Inventors: Morihito Ikeda, Ashigarakami-gun (JP);
Taisei Nishimi, Ashigarakami-gun (JP);
Junichi Katada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

(21) Appl. No.: 12/934,322

(22) PCT Filed: Mar. 13, 2009

(86) PCT No.: PCT/JP2009/054950
§ 371 (c)(1),
(2), (4) Date: Sep. 24, 2010

(87) PCT Pub. No.: WO2009/119355
PCT Pub. Date: Oct. 1, 2009

(65) Prior Publication Data
US 2011/0020649 A1    Jan. 27, 2011

(30) Foreign Application Priority Data

Mar. 24, 2008  (JP) ................. 2008-076724
Mar. 24, 2008  (JP) ................. 2008-076725

(51) Int. Cl.
*C40B 60/00*    (2006.01)
(52) U.S. Cl. .......................... 506/33; 422/400; 422/425
(58) Field of Classification Search ............... 422/400, 422/425; 506/33
See application file for complete search history.

(56) References Cited

U.S. PATENT DOCUMENTS
7,195,924 B2    3/2007   Hwang et al.
2003/0104397 A1    6/2003   Lefkowitz et al.
(Continued)

FOREIGN PATENT DOCUMENTS
CA    2133946    *    4/2006
CA    2133946 C        4/2006
(Continued)

OTHER PUBLICATIONS

Wlad Kusnezow et al., "Antibody microarrays: An evaluation of production parameters", Proteomics, 2003, pp. 254-264, vol. 3.

(Continued)

*Primary Examiner* — Jill Warden
*Assistant Examiner* — Monique Cole
(74) *Attorney, Agent, or Firm* — Sughrue Mion, PLLC

(57) ABSTRACT

An immobilization method for immobilizing a physiologically active substance on a solid phase carrier, the method including: bringing the solid phase carrier into contact with an acid anhydride functional group-containing silane coupling agent represented by the following Formula (I); and carrying out a process of binding of the physiologically active substance to the acid anhydride functional group while maintaining the solid phase carrier after the contact at a temperature within the range of 0° C. to 60° C.; a physiologically active substance-immobilized carrier, and a carrier for immobilization are provided. Further, a carrier including a porous material treated with an acid anhydride functional group-containing silane coupling agent represented by the following Formula (I), a blocking agent that is immobilized to the porous material; and a method for producing it is provided.

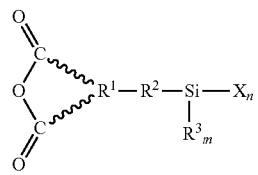

15 Claims, 4 Drawing Sheets

U.S. PATENT DOCUMENTS

| | | |
|---|---|---|
| 2006/0029961 A1 | 2/2006 | Goh |
| 2006/0110594 A1 | 5/2006 | Frutos |
| 2008/0188010 A1 | 8/2008 | Saitoh et al. |

FOREIGN PATENT DOCUMENTS

| | | |
|---|---|---|
| EP | 0 653 429 A1 | 5/1995 |
| EP | 1 553 415 A1 | 7/2005 |
| EP | 1 801 238 A1 | 6/2007 |
| JP | 6-148190 A | 5/1994 |
| JP | 7-188259 A | 7/1995 |
| JP | 8-506902 T | 7/1996 |
| JP | 2005-201901 A | 7/2005 |
| JP | 2007-078399 A | 3/2007 |
| JP | 2007-114018 A | 5/2007 |
| JP | 2007-536527 A | 12/2007 |
| JP | 2008-209379 A | 9/2008 |
| WO | 2006/012744 A1 | 2/2006 |
| WO | 2006/058237 A2 | 6/2006 |

OTHER PUBLICATIONS

Supplementary European Search Report dated Jan. 24, 2013 in European Patent Application No. 09725388.4.

Office Action dated Jan. 22, 2013 in Japanese Patent Application No. JP 2008-076725.

Office Action dated Feb. 12, 2013 in Japanese Patent Application No. 2008-76724.

* cited by examiner

METHOD FOR IMMOBILIZATION, PHYSIOLOGICALLY ACTIVE SUBSTANCE-IMMOBILIZED CARRIER, CARRIER FOR IMMOBILIZATION, CARRIER, AND PROCESS FOR PRODUCING CARRIER

TECHNICAL FIELD

The present invention relates to an immobilization method, physiologically active substance-immobilized carrier, carrier for immobilization, carrier, and process for producing a carrier.

BACKGROUND ART

Diagnostic chips, and biochemical reaction chips using solid phase carriers such as protein microarrays are very useful in the field of research and development and the clinical field. For example, in terms of a protein microarray or the like, a protein solution is brought into contact with a glass substrate to immobilize the protein on the substrate, and using the physiological activity of the immobilized protein, diagnosis or analysis is carried out. In this case, it is required that the protein can be immobilized at a high density and that the substance to be reacted with the immobilized protein not adsorb nonspecifically to the carrier.

To eliminate such non-specific adsorption, for example, in Proteomics, (2003) Vol. 3, pp. 254-264, a method wherein a protein is directly adsorbed and immobilized via a polylysine coating layer or an amino group layer and a method wherein a protein is immobilized by covalent bonding via an active ester layer formed by a multistep reaction are described.

Further, in Japanese Patent Application Laid-Open (JP-A) No. 2005-201901, a method is described wherein a substrate is directly carboxylated using a particular silane coupling agent and thereby activated to allow a protein to be covalently bound to the substrate. In cases where a silane coupling agent such as the one disclosed in JP-A 2005-201901 is used, in general, after coating a substrate with the silane coupling agent, the coating is solidified by a baking treatment at a temperature of not less than 100° C. to form a three dimensional network structure.

In such a method, although it is possible to immobilize a protein stably at a relatively high density, the density at which the protein is immobilized is not sufficient, and non-specific adsorption of the substrate to be reacted with the immobilized protein increases.

Further, in order to increase the amount of immobilization of a physically active ligand such as a protein, a solid phase carrier having a porous structure such as a non-woven fabric structure of fibers or a particle-packed structure is used.

For example, in JP 6-148190 A, a biochemical assay is carried out by allowing an acid anhydride to be covalently bound to a porous membrane. Further, in JP 8-506902 A, a biochemical assay is carried out by immobilizing an acid anhydride-containing polymer and a protein on a porous solid phase including glass-fiber paper. Further, in WO 2006/058237, an acid anhydride-containing polymer and a protein are immobilized, and when a biochemical assay is carried out, a blocking agent is used, thereby suppressing non-specific adsorption.

[Patent Document 1] JP-A 2005-201901
[Patent Document 2] JP-A 6-148190
[Patent Document 3] JP-A 8-506902
[Patent Document 4] WO 2006/058237

[Non-patent Document 1] Proteomics, (2003) Vol. 3, pp. 254-264

DISCLOSURE OF THE INVENTION

Problems to be Solved by the Invention

An object of one mode of the present invention is to provide an immobilization method in which the amount of non-specific adsorption is small and a sufficient amount of a physiologically active substance can be immobilized, a physiologically active substance-immobilized carrier, and a carrier for immobilization.

On the other hand, when the surface area is increased using a porous structure, non-specific adsorption, as well as the amount of immobilization of the ligand, tends to increase. In general, usage of a blocking agent lead to suppression of non-specific adsorption, but the ratio between the binding signal (S) by a large amount of immobilization of a ligand and the background by the non-specific adsorption suppression capacity, that is, the S/N ratio, did not increase.

Thus, an object of another mode of the present invention is to provide a carrier not only with which the amount of non-specific adsorption is suppressed, but also with which the ratio between the signal of binding to a ligand and the background is enhanced by the nonspecific-adsorption-suppression capacity (S/N ratio), and a method for producing the carrier.

Means for Solving the Problems

In the first mode of the present invention, an immobilization method for immobilizing a physiologically active substance on a solid phase carrier, the method including: bringing the solid phase carrier into contact with an acid anhydride functional group-containing silane coupling agent represented by the following Formula (I); and carrying out a process of binding of the physiologically active substance to the acid anhydride functional group while maintaining the solid phase carrier after the contact at a temperature within the range of 0° C. to 60° C.; is provided.

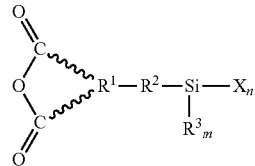

(I)

In Formula (I), $R^1$ represents a trivalent linear or branched aliphatic group or aromatic group; $R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group; $R^3$ represents a hydrogen atom or a $C_1$ to $C_{10}$ alkyl group; X represents an alkoxy group (—$OR^4$), a halogen atom or an acyloxy group (—$OOCR^5$), wherein $R^4$ and $R^5$ each independently represent a hydrogen atom or a $C_1$ to $C_{10}$ alkyl group; n represents 1, 2 or 3; and m represents an integer of (3-n).

Further, a physiologically-active-substance-immobilized carrier in which a physiologically active substance was immobilized on a solid phase carrier by the above immobilization method is provided.

Further, a carrier for immobilization obtained by bringing the solid phase carrier into contact with an acid anhydride functional group-containing silane coupling agent represented by Formula (I) above, and used for preparing the above physiologically-active-substance-immobilized carrier is provided.

In the second mode of the present invention, a carrier including a porous material treated with an acid anhydride functional group-containing silane coupling agent represented by the following Formula (I), a blocking agent that is immobilized to the porous material is provided.

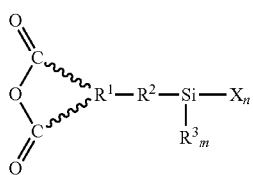

(I)

In Formula (I), $R^1$ represents a trivalent linear or branched aliphatic group or aromatic group; $R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group; $R^3$ represents a hydrogen atom or a $C_1$ to $C_{10}$ alkyl group having; X represents an alkoxy group (—$OR^4$), a halogen atom or an acyloxy group (—$OOCR^5$), wherein $R^4$ and $R^5$ each independently represent a hydrogen atom or a $C_1$ to $C_{10}$ alkyl group; n represents 1, 2 or 3; and m represents an integer of (3-n).

Further, a method for producing a carrier, the method including: treating a porous material with an acid anhydride functional group-containing silane coupling agent represented by Formula (I) above; and bringing the porous material treated with the silane coupling agent into contact with a blocking agent; is provided.

Effect of the Invention

By the first mode of the present invention, an immobilization method, a physiologically active substance-immobilized carrier, and a carrier for immobilization, with which the amount of non-specific adsorption can be kept small and a sufficient amount of a physiologically active substance can be immobilized, can be provided.

Further, by the second mode of the present invention, a carrier not only with which the amount of non-specific adsorption is suppressed, but also which shows an enhanced S/N ratio, and a method for producing it can be provided.

BEST MODE FOR CARRYING OUT OF THE INVENTION

Figure 1A:
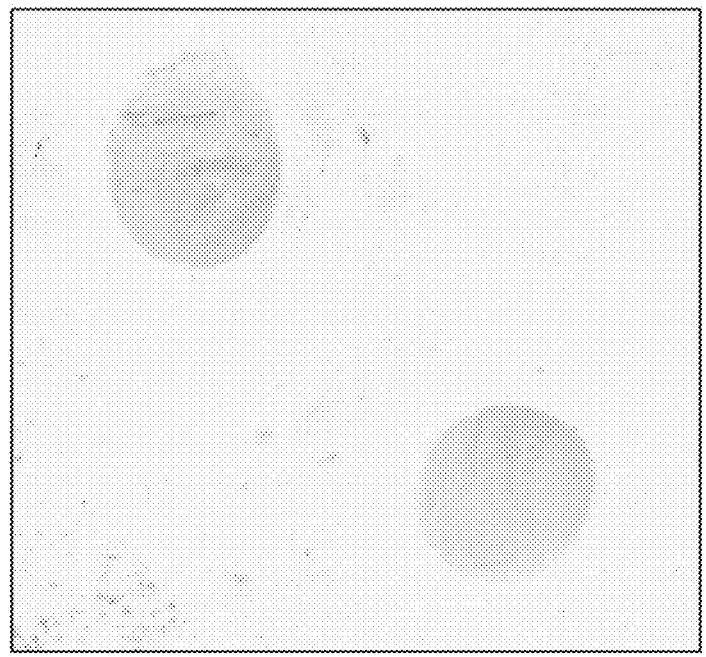
FIG. 1A shows a fluorograph of the physiologically active substance-immobilized carrier (antigen concentration: 1 nM) of Example 17.

1. Method for Immobilization, Physiologically Active Substance-Immobilized Carrier and Carrier for Immobilization A method for immobilization, physiologically active substance-immobilized carrier and carrier for immobilization according to the first mode of the present invention (hereinafter, in this section "1. Method for Immobilization, Physiologically Active Substance-Immobilized Carrier and Carrier for Immobilization", they may also be referred to as "a method for immobilization of the present invention", "a physiologically active substance-immobilized carrier of the present invention" and "a carrier for immobilization of the present invention", respectively) are described.

The method for immobilization according to the first mode of the present invention is a method for immobilizing a physiologically active substance on a solid phase carrier, the method including bringing the solid phase carrier into contact with an acid anhydride functional group-containing silane coupling agent represented by Formula (I) (contacting step) and carrying out a treatment for binding of the physiologically active substance to the acid anhydride functional group while maintaining solid phase carrier(s) after the contact at a temperature within the range of 0° C. to 60° C. (treatment for binding).

In this method for immobilization, after a specific acid anhydride functional group-containing silane coupling agent is brought into contact with the solid phase carrier, the physiologically active substance is bound while maintaining the solid phase carrier at a temperature within the range of 0° C. and 60° C. That is, without a baking treatment at 100° C. or higher which is commonly carried out for immobilizing the silane coupling agent on the solid phase carrier, the treatment for binding of the physiologically active substance is carried out. Accordingly, the silane coupling agent is brought into contact to the solid phase carrier but the baking treatment is not carried out; and therefore non-specific adsorption can be significantly suppressed. In addition to this, by carrying out the treatment for binding of the physiologically active substance to the acid anhydride, a sufficient amount of physiologically active substance can be immobilized. Without being specifically bound by any theory, since the baking is not carried out in this method for immobilization, it is presumably reasoned that, by effectively reducing stains brought about by a reaction between an acid anhydride and foreign particle during the baking, non-specific adsorption can be suppressed.

The solid phase carrier used in the present invention is not particularly restricted as long as it is a commonly used one.

Any form of a planar substrate, a substrate with irregularity, a substrate with rough surface, a particle, a fine particle, a rod-like particle, a thin membrane, a fiber, a column, mesh or a probe tip can be selected. The materials of the solid phase carrier are not restricted as long as they are materials capable of forming metal(silicon)-oxygen-silicon-carbon bonds by a silane coupling reaction. Specifically, glass; oxides such as silica, alumina, titania, zirconia or indium tin oxides (ITO); or nitrides such as silicon nitride, gallium nitride, aluminum nitride or indium nitride can be used individually or as a complex thereof.

Further, as long as the outermost layer is made of a material capable of forming the bond by the silane coupling reaction, a solid phase carrier per se may be a multilayer structure body using silicone, various metals or polymers. A method for forming the material with a silane coupling reactivity on the outermost layer is not particularly restricted as long as it is a method in accordance with a general method for modifying a surface; and specific examples thereof include formation of thin film in a gaseous phase such as physical vapor deposition or chemical vapor deposition (CVD) sputtering; formation of thin film in a liquid phase by sol-gel method or the like; modification of the vicinities of the surface, such as surface oxidation or the like; and the like. Among them, from the viewpoint of stability of the carrier itself, glass or silica carriers are preferable. Also, because of easiness of processing, carriers with a silica thin film layer being formed on the surface of polymer are preferred and, from the viewpoint of flatness, carriers obtained by the surface of a silicon single-crystalline surface is subjected to the surface oxidation are preferred.

An acid anhydride functional group-containing silane coupling agent represented by the above-mentioned Formula (I) is described in "3. Acid Anhydride Functional Group-Containing Silane Coupling Agent".

When a silane coupling agent is brought into contact with a solid phase carrier, the silane coupling agent may be used in the form of an original liquid as is or an appropriate solution. From the viewpoint of performing thin and uniform surface modification, a solution of 0.01% by mass to 10% by mass, more preferably a solution of 0.1% by mass to 2% by mass is selected.

As for the type of solvents, any of polar solvents and nonpolar solvents can be used. Examples of the polar solvents include ethanol, methanol, water and the like. Also, examples of the nonpolar solvents include aliphatic hydrocarbon based solvents such as hexane, octane or cyclohexane; aromatic hydrocarbon based solvents such as benzene, xylene or toluene; ether based solvents such as diethyl ether; chlorine based solvents such as chloroform or methylene chloride; ester based solvents such as ethyl acetate; and the like. The solvent can be appropriately selected among the polar solvents and nonpolar solvents based on solvent tolerance of the solid phase carrier or the like. For example, hexane, ethanol or the like can be appropriately selected.

As the solvent in the present invention, in order to allow dehydration condensation to effectively progress without carrying out a baking treatment, nonpolar solvents are preferred. Among them, toluene or xylene is preferred.

In a contacting step, a treatment for contacting between a solid phase carrier and a silane coupling agent is carried out. It is speculated that, by this contact, a hydrogen bond is formed between the silane coupling agent having a silanol group and a hydroxyl group of the solid phase carrier by hydrolysis and subsequently dehydration condensation takes place, thereby forming a strong bond. Complete dehydration condensation does not have to proceed. And, even in cases where the dehydration condensation does not completely proceed, the resultant can be used as is depending on an object.

Hydrolysis of the silane coupling agent may be in advance carried out before the silane coupling agent is brought into contact with the solid phase carrier. The hydrolysis and binding may continually proceed at the same time during the contacting step. A method of allowing hydrolysis and binding to continually proceed at the same time during the contacting step is more preferred. This simultaneously progressed treatment can be easily achieved simply by dissolving the silane coupling agent before the hydrolysis in a solvent and bringing the resulting solution into contact to the solid phase carrier.

Water for hydrolysis may be added to a solution of silane coupling agent. Yet, it is often the case that water adsorbed to a solid phase carrier or water infiltrated from the air is sufficient. Therefore, in order to increase efficiency of the subsequent dehydration condensation reaction, it is preferred that water be not added. Further, it is preferred that as much water dissolving in a solvent as possible be removed.

Such contact is not particularly restricted as long as a silane coupling agent, as is or as a solution thereof dissolved in a solvent, can be brought into contact on a solid phase carrier. Specific examples thereof include an immersion method wherein the solid phase carrier is immersed in a solution of the silane coupling agent for an appropriate period of time and then taken out of the solution. In this immersion method, a dehydration condensation reaction can progress during the contacting step. Thus, even if the silane coupling agent adsorbed in the solid phase carrier is washed away after the solid phase carrier is taken out of the solution, only the bound silane coupling agent can remain. As a result, it is possible to carry out thin and uniform surface modification. Also, since it can be employed regardless of the form of solid phase carrier, versatility thereof is high.

Example of the method for contacting further include a method wherein the silane coupling agent as it or a solution thereof dissolved in a solvent is coated. As the method for coating, a known method can be used. Specifically, an extrusion coating method, a curtain coating method, a casting method, a screen printing method, a spin coating method, a spray coating method, a slide-bead coating method, a slit and spin method, a slit coating method, a die coating method, a dip coating method, a knife coating method, a blade coating method, a flow coating method, a roll coating method, a wire bar coating method, a transfer printing method or the like can be used. These methods for forming a thin film are described in "Developments in Coating Technology" or "Koteingu Gijutsu no Shinpo", Yuji Harasaki, Sogo Gijutsu Center (1988); "Coating Technology" or "Koteingu Gijutsu" Technical Information Institute Co., Ltd. (1999); "Technology of Water-Borne Coatings" or "Suisei Koteingu no Gijutsu" CMC (2001); "Evolving Organic Thin Film, Formation" or "Shinkasuru Yuuki Hakumaku Seimaku Hen" S. B. Research Co., Ltd. (2004); "Polymer Surface Processing" or "Koubunshi Hyoumen Kakougaku", Satoru Iwamori, Gihodo Shuppan Co., Ltd. (2005); or the like. Since it is possible to easily produce a coating film whose thickness is controlled, a method for coating on a flat solid phase carrier in the present invention is preferably a spray coating method or a spin coating method, and more preferably a spin coating method. The spin coating method may be carried out at 300 rpm to 10000 rpm. In order to perform thin and uniform surface modification, it is preferred to be not less than 1000 rpm.

When a contacting step is performed by coating, since efficiency of the progress of dehydration condensation is low during the coating step, it is preferred that treatment for binding of a physiologically active substance be carried out without carrying out washing immediately after the coating. Also, both in an immersion method and coating method, in cases where a polar solvent is used as a solvent, it is preferred that the treatment for binding of the physiologically active substance be carried out without carrying out washing after the contacting step because the efficiency of dehydration condensation is generally low. Yet, in cases where the contacting treatment is carried out using a nonpolar solvent for not less than 10 minutes, the washing may be carried out for the purpose of homogenization of a silane coupling agent reaction.

The contacting treatment may be continued until an acid anhydride functional group is held by a solid phase carrier. From the viewpoint of preventing decomposition of an acid anhydride by hydrolysis with time or unevenness of a silane coupling agent by increasing the number of layers, it is preferred to be less than 3 hours. From the viewpoint of efficiency of the treatment, it is more preferred to be less than 2 hours, still more preferably not more than 1 hour.

In a binding step, if the treatment for binding is carried out under a high temperature environment, an acid anhydride functional group in activated state thereof interacts with a substance in a surrounding environment, and therefore a chemical structure of interest cannot be maintained and non-specific adsorption increases. For example, by binding of an organic substance contained in the air with the acid anhydride functional group, the organic substance is adsorbed to a solid phase carrier as a stain. Because of this, it is required that the treatment for binding of a physiologically active substance to the acid anhydride functional group be carried out while maintaining the solid phase carrier after the process of contacting at a temperature in the range of 0° C. and 60° C., and it is more preferred that the solid phase carrier is held from 0° C. to 40° C. In this case, in addition to the time point when the physiologically active substance is made to bond, the silane solid phase carrier is consistently hold in such a temperature region all through a period after the contact of the silane coupling agent to the binding step. That is, in the silane coupling reaction, a baking treatment which is commonly carried out is not carried out.

Further, as described below, in cases where the physiologically active substance is directly brought into contact and bind to a succinic anhydride functional group, the acid anhydride functional group is decomposed by being exposed to high temperature and the sufficient amount of the physiologically active substance is not immobilized. Thus, also from this purpose, it is necessary to maintain such a temperature region.

The binding of a physiologically active substance may be carried out by a method wherein an acid anhydride functional group is once hydrolyzed to a carboxyl group and then the physiologically active substance is brought into contact to the carboxyl group which has been further activated, thereby immobilizing the physiologically active substance. Yet, from the viewpoint of suppressing non-specific adsorption, it is preferred that, without carrying out the treatment for activating of the surface of the solid phase carrier or the like, the physiologically active substance be directly brought into contact to an acid anhydride functional group on the surface of the solid phase carrier and then immobilized. By this method, since the number of steps and time before and after the activation can be decreased, changes of a chemical state (such as adsorption) by a disturbance factor can be suppressed. Therefore, non-specific adsorption can be significantly suppressed.

The term "treatment for activating" herein refers to a treatment wherein an activator is allowed to react to a carboxyl group derived from an acid anhydride functional group on the surface of a solid phase carrier after a process of contacting, thereby rendering an activated state. Examples of activators used herein include carbodiimide and derivatives thereof. Specific examples include 1-ethyl-3-(3-dimethylaminopropyl)carbodiimide (EDC), 1-ethyl-3-(3-dimethylaminopropyl)carbodiimide (EDC) hydrochloride, N,N'-dicyclohexyl-carbodiimide(DCC) and N,N'-diisopropylcarbodiimide (DIC). Further, in order to improve reactivity and reaction stability, succinimide or the like can be used in combination therewith. Specific examples thereof include N-hydroxysuccinimide (NHS), N-hydroxysulfosuccinimide (Sulfo-NHS), 3,4-dihydro-3-hydroxy-4-oxo-1,2,3-benzotriazine (Dhbt) and the like.

A physiologically active substance is described in "4. Physiologically Active Substance".

In the treatment for binding, a physiologically active substance is used as an aqueous solution thereof dissolved in an appropriate aqueous solvent (hereinafter, referred to as a physiologically active substance-containing solution). As the aqueous solvent which can be used here, a common solution used as a solvent of the physiologically active substance can be used as is. And, examples thereof include water, saline, acetate buffer, citrate buffer, phosphate buffer, HEPES buffer (4-(2-hydroxyethyl)-1-piperazineethanesulfonic acid), MES buffer (2-(N-morpholino)ethanesulfonic acid) and the like. In the treatment for binding, since an acid anhydride functional group or a functional group thereof which is hydrolyzed•activated has in general a high reactivity with a nucleophilic functional group, buffers containing amines such as Tris buffer (trihydroxymethylaminomethane) are not preferred.

In cases where a physiologically active substance has a charge opposite to that of the surface of the solid phase carrier, it is concentrated on the surface of the solid phase carrier and efficiency of binding thereof increases. Since the acid anhydride functional group has a carboxyl group when a part thereof is decomposed, it is thought that the surface thereof is negatively-charged in the case of contacting a solution of a pH of not less than about 3. Because of this, in cases where the pH of the solution is lower than the isoelectric point of the physiologically active substance and not less than 3, the physiologically active substance is positively-charged in the solution and the physiologically active substance has the charge opposite to that of the surface of the carrier. Thus, the efficiency of binding thereof is enhanced. It is therefore preferred that the pH of the solution be not less than 3 and less than the isoelectric point of the physiologically active substance from the point of view that the amount of binding can be increased.

After the treatment for binding, from the viewpoint of suppressing non-specific adsorption, it is preferred to carry out a hydrolysis treatment. Since, by this hydrolysis treatment, an unreacted acid anhydride functional group is converted to a carboxyl group, non-specific adsorption is effectively suppressed.

The hydrolysis treatment can be carried out by a conventional known method wherein an acid anhydride functional group is decomposed to generate a carboxyl group. It is generally carried out using an aqueous solution of 20° C. to 100° C. In order to thoroughly complete the hydrolysis reaction, it is preferred that an alkaline or acidic aqueous solution be used. In particular, it is more preferred that an alkaline aqueous solution of a pH of not less than 10 be used. Specific examples thereof include 1 mM to 1 M aqueous NaOH solution, aqueous KOH solution and the like. In this case, due to high reactivity, a treatment within 10 minutes is sufficient.

Yet, from the viewpoint of maintaining activity of the bound physiologically active substance, a mild aqueous solution of a pH of 5 to 9 is preferably used. Specific examples thereof include pure water, borate buffer, citrate buffer, phosphate buffer, HEPES buffer, acetate buffer and the like. Furthermore, from the viewpoint of easy operation, a method of holding in a vapor atmosphere can also be exemplified. In the case of these mild methods, it is preferred to treat for not less than 10 minutes. By this, two carboxyl groups are produced from the acid anhydride functional group. As an index for progress of the hydrolysis treatment, a method for measuring a contact angle to water of the solid phase carrier or the like after the treatment can be exemplified.

For the above-mentioned physiologically active substance-immobilized carrier, in cases where an ability to suppress non-specific adsorption is not satisfactory, such as a case where the pH is low, in addition to a physiologically active substance, a blocking agent can be immobilized to the above-mentioned carrier. That is, the method for immobilization of the present invention may be a method including immobilizing the blocking agent on a solid phase carrier after contacting with a silane coupling agent. The blocking agent refers to a substance having an ability to suppress adsorption of a substance that is a subjected of suppression of non-specific adsorption. Based on the type of the subject of the suppression or the like, an appropriate substance can be selected as the blocking agent.

Examples of blocking agents include water-soluble proteins, water-soluble polymers and the like. Preferred examples of the water-soluble proteins include albumin, casein, gelatin and the like. From the viewpoint of an ability to suppress non-specific adsorption, the blocking agent is more preferred to be albumin or casein. Preferred examples of the water-soluble polymers include polyethylene glycol, phosphorylcholine group-containing polymers, polysaccharides, polyvinyl alcohol, polyhydroxy ethyl methacrylate, polyacrylic acid, polyacrylamide, zwitter ion-containing polymers, polyvinylpyrrolidone and the like. From the viewpoint of an ability to suppress non-specific adsorption, the blocking agent is preferred to be polyethylene glycol, phosphorylcholine group-containing polymers, dextran, carboxymethyl dextran or dextran sulfate.

Also, in cases where these water-soluble polymers are used, in order to improve ability to immobilize on the above-mentioned carrier, the water-soluble polymers may have a moiety binding with or adsorbed to a carrier. The moiety binding with the carrier is not particularly restricted as long as it is a structure binding with an acid anhydride and specific examples thereof include functional groups having amines such as primary amines. Also, examples of the moiety adsorbing to the carrier include a structure adsorbing to the carrier by electrostatic interaction, a structure positively-charged at the pH of the immobilization; more specifically polyallylamine, polyethyleneimine, polyvinylamine, polylysine, derivatives thereof, and the like. As the water-soluble polymer having such a structure, NanoBio Blocker manufactured by NaoBio Tech can preferably be used.

In the carrier, the part thereof to which a blocking agent is immobilized may be the same part as where a physiologically active substance was in advance immobilized, that is, a space to which the physiologically active substance is not immobilized even after carrying out the treatment for immobilization; a part to which the treatment for immobilization of the physiologically active substance was not carried out in the carrier; and both of them. Further, the timing to carry out the treatment for immobilization of the blocking agent is not particularly restricted. Examples thereof include a time point immediately after the immobilization of the physiologically active substance, a time point after the hydrolysis treatment, and the same time point as the immobilization of the physiologically active substance. It is possible to simultaneously carry out the hydrolysis treatment by carrying out the immobilization of the blocking agent after the immobilization of the physiologically active substance.

The thus obtained physiologically active substance-immobilized carrier has a surface onto which the sufficient amount of the physiologically active substance can be immobilized. The amount of physiologically active substance immobilized to the surface of the carrier can be checked by a method usually used for this purpose. Examples thereof include a method for measuring fluorescence using a fluorescent substance, SPR (surface plasmon resonance), LPR (local plasmon resonance), QCM (quartz crystal microbalance) and the like.

The physiologically active substance-immobilized carrier of the present invention is one in which a physiologically active substance is immobilized to a solid phase carrier by the above-mentioned method for immobilization.

In this physiologically active substance-immobilized carrier, the physiologically active substance may be immobilized at a high density and, further, exhibits significantly low non-specific adsorption. Hence, it is useful for detection and analysis of molecules specific to the physiologically active substance on the carrier. In particular, it is suitable for a variety of microarrays, biosensors or the like, which require high specificity for the physiologically active substance, such as analysis of a trace amount or detection of minute interaction.

The carrier for immobilization of the present invention is one obtained by bringing the above-mentioned solid phase carrier into contact with the acid anhydride functional group-containing silane coupling agent represented by the above-mentioned Formula (I), and may have an acid anhydride functional group at a high density in the surface thereof. In cases where a desired physiologically active substance is immobilized to the acid anhydride functional group on the surface of this carrier for immobilization, it can have the physiologically active substance at a high density on the surface thereof and, further, the carrier for immobilization with significantly low non-specific adsorption carrier can be provided. Because of this, the carrier for immobilization of the invention is useful as a material to prepare the an immobilized carrier for applications requiring high specificity to the physiologically active substance.

2. Carrier and Method for Production Thereof

A carrier and a method for production thereof according to the second mode of the present invention (hereinafter, in this section "2. Carrier and Method for Production Thereof", they may also be referred to as "a carrier of the present invention" and "a method for producing a carrier of the present invention", respectively) will be described.

The carrier according to the second mode of the present invention is a carrier including a porous material which is treated with an acid anhydride-containing silane coupling agent represented by the above-mentioned Formula (I) and to which a blocking agent is immobilized.

In the present invention, in cases where the porous material is used as a solid phase carrier, combining the silane coupling agent represented by Formula (I) with the blocking agent makes it possible to not only simply suppress non-specific adsorption but also enhance a binding signal with respect to a ligand, thereby sufficiently improving an S/N ratio.

The form of a carrier of the present invention is not particularly restricted as long as it is one containing a form of porous material at least in a part thereof. And, any form of a membrane, a filter, a particle-filled structure, a column, a fiber, a hollow fiber, a fine porous material structure, a planar substrate, a substrate with irregularity, a substrate with rough surface or the like can be selected.

Examples of the materials used in the surface of the carrier of the present invention include inorganic materials capable of forming metal (silicon)-oxygen-silicon-carbon bonds by a silane coupling reaction. Specifically, glass; inorganic oxides such as silica, alumina, titania, zirconia or indium tin oxides (ITO); or inorganic nitrides such as silicon nitride, gallium nitride, aluminum nitride or indium nitride can be used individually or as a complex thereof. Furthermore, as long as the outermost layer is made of the above-mentioned material capable of forming the bond by the silane coupling reaction, a solid phase carrier per se may be a multilayer structure using silicone, various metals or polymers.

A method for forming a material with silane coupling reactivity in the outermost layer is not particularly restricted as long as it is a method in accordance with a common method for modifying a surface and specific examples thereof include formation of thin film in a gaseous phase such as physical vapor deposition or chemical vapor deposition (CVD) sputtering; formation of thin film in a liquid phase by sol-gel method, plating method or the like; modification of the vicinities of the surface by surface oxidation or the like; and the like as well as a combination thereof. Also, similarly, as long as at least a part of the outermost layer is a form of porous material any form may be employed. And, a complex with a structure which is not a porous material may also be employed.

Among them, preferred specific examples thereof include glass filter (glass fiber nonwoven fabric), silica bead-filled column, anodizing alumina coating film, mesoporous silica carrier, and the like.

The form such as size and thickness as well as the pore diameter of a porous material used for a carrier are not particularly restricted. From the point of view that a surface area is improved and clogging of pores by a reaction is not prevented, as for the pore diameter, it is generally preferred to be about 1 nm to 1 mm, more preferably about 10 nm to 100 µm as an average pore diameter. In the present description, the "pore diameter" of the porous material refers to a diameter in cases where the shape of the pore is circular while it means the maximum diameter in cases where the shape thereof is rectangle. This "pore diameter" can be calculated from microscope such as AFM or, in the case of a complicated shape, from capture capability of particles or the like.

As a method for calculating the pore diameter from the capture capability of particles or the like, for example, the following latex method can be used. The latex method is a method wherein the porous material is immersed in a solvent; 0.01% by mass uniform latex solution (example: latex of a diameter of 1 µm) is subjected to suction filtration; the absorbance of the filtrate at 600 nm is measured by a spectrophotometer; from a ratio thereof to the absorbance of the original solution, a capture ratio is calculated; and a particle diameter at which the capture ratio reaches 99.9% by mass is defined as a pore diameter derived from the capture capability.

As for the pore diameter in the present invention, at least one of a value measured by the microscope such as AFM and a value obtained from the capture capability of the particle is within the above-mentioned range.

An acid anhydride functional group-containing silane coupling agent represented by Formula (I) will be described in "3. Acid Anhydride Functional Group-Containing Silane Coupling Agent".

Examples of the blocking agent of the present invention include a molecule containing a water-soluble protein or water-soluble polymer. Preferred examples of the water-soluble protein include albumin, casein, gelatin and the like. From the viewpoint of an ability to suppress non-specific adsorption, it is more preferred to be albumin or casein. Preferred examples of the water-soluble polymer include polyethylene glycol, phosphorylcholine group-containing polymers, polysaccharides, polyvinyl alcohol, polyhydroxy ethyl methacrylate, polyacrylic acid, polyacrylamide, zwitter ion-containing polymers, polyvinylpyrrolidone and the like. From the viewpoint of ability to suppress non-specific adsorption, it is preferred to be polyethylene glycol, phosphorylcholine group-containing polymers, dextran, carboxymethyl dextran or dextran sulfate. These water-soluble proteins and water-soluble polymers may be used individually or in combination. Also, in addition to one containing such a molecule as a simple substance, one containing the molecule as a partial structure may be employed.

Also, in cases where these water-soluble polymers are used, in order to improve ability to immobilize on the above-mentioned porous material, the water-soluble polymers may have a moiety binding with or adsorbed to a porous material. The moiety binding with the porous material may be a structure binding and adsorbing to an acid anhydride such as amines. The moiety binding with the porous material may be a hydrophobic moiety which does not play an active role in binding and adsorption. From the viewpoint of allowing stable adsorption with a carboxyl group which is a group resulting from hydrolysis of the acid anhydride, a structure adsorbing to the porous material by multipoint electrostatic interactions can be exemplified. Specific examples include a structure having plural positive charges at the pH of the immobilization; more specifically polyallylamine, polyethyleneimine, polyvinylamine, polylysine, derivatives thereof, and the like. As the water-soluble polymer having such a structure, NanoBio Blocker manufactured by NaoBio Tech can preferably be used.

In the above-mentioned porous material, a part to which a blocking agent is immobilized may be the same part as where a physiologically active substance was in advance immobilized, that is, a space to which the physiologically active substance is not immobilized even after carrying out the treatment for immobilization; a part on which the treatment for immobilization of the physiologically active substance was not carried out in the porous material; and both of them.

It is preferred that a physiologically active substance be immobilized to a porous material used for the carrier of the present invention. The physiologically active substance is described in "4. Physiologically Active Substance".

The physiologically active substance is immobilized to a porous material after a treatment with the above-mentioned silane coupling agent and preferably reacts to bind with an acid anhydride functional group present on the porous material after the process with the above-mentioned silane coupling agent.

The carrier of the present invention can be obtained by a method of production including treating the above-mentioned porous material with the above-mentioned acid anhydride containing silane coupling agent and bringing a blocking agent into contact to the porous material treated with the silane coupling agent.

The treatment with the silane coupling agent may be attained by bringing the porous material into contact with the silane coupling agent. It is speculated that, by this contact, a hydrogen bond is formed between the silane coupling agent having a silanol group and a hydroxyl group of the porous material by hydrolysis and subsequently dehydration condensation takes place, thereby forming a strong bond. Complete dehydration condensation does not have to proceed. And, even in cases where the dehydration condensation does not completely proceed, the resultant can be used as is depending on an object.

When a porous material is treated with a silane coupling agent in the present invention, the above-mentioned porous material is brought into contact with the silane coupling agent. When brought into contact, the silane coupling agent may be used in the form of an original liquid as is or an appropriate solution. From the viewpoint of performing thin and uniform surface modification, a solution of 0.01% by mass to 10% by mass, more preferably a solution of 0.1% by mass to 2% by mass is selected.

As for the type of solvents, any of polar solvents and nonpolar solvents can be used. Examples of the polar solvents include ethanol, methanol, water and the like. Also, examples of the nonpolar solvents include aliphatic hydrocarbon based solvents such as hexane, octane or cyclohexane; aromatic hydrocarbon based solvents such as benzene, xylene or toluene; ether based solvents such as diethyl ether; chlorine based solvents such as chloroform or methylene chloride; ester based solvents such as ethyl acetate; and the like. The solvent can be appropriately selected among the polar solvents and nonpolar solvents based on solvent tolerance of the porous material or the like. For example, hexane, ethanol or the like can be appropriately selected. Among them, from the viewpoint of allowing dehydration condensation to effectively proceed without carrying out a process of baking, nonpolar solvents are preferred. Among them, toluene or xylene is preferred.

Such contact is not particularly restricted as long as a silane coupling agent, as is or as a solution thereof dissolved in a solvent, is brought into contact on a porous material. Specific examples include an immersion method wherein the porous material is immersed in a solution of the silane coupling agent for an appropriate period of time and then taken out of the solution. In this immersion method, a dehydration condensation reaction can progress during the contacting step. Thus, even if the silane coupling agent adsorbed to the surface of the porous material is washed away after the porous material is taken out of the solution, only the bound silane coupling agent can remain. As a result, it is possible to carry out thin and uniform surface modification without changing a pore diameter. Also, since this method can be employed regardless of the form of the porous material, versatility thereof is high.

When a silane coupling agent is washed away, it is preferred that a volatile solvent be used as a washing liquid at least for the last wash. This is because the washing liquid tends to remain in the porous material and there is a possibility that this residual washing liquid may inhibit a subsequent reaction or decrease activity of a physiologically active substance to be immobilized. Examples of the volatile solvent include acetone, diethyl ether, acetonitrile, hexane, methanol, ethanol and the like. And, because of no reactivity and appropriate volatility thereof, acetone, diethyl ether or acetonitrile is preferably used.

The contacting treatment may be continued until an acid anhydride functional group is held by a porous material. From the viewpoint of preventing decomposition of an acid anhydride by hydrolysis with time or unevenness of a silane coupling agent by increasing the number of the layers, it is preferred to be less than 3 hours. From the viewpoint of efficiency of the treatment, it is more preferred to be less than 2 hours, still more preferably not more than 1 hour. Since in general there are some cases where the porous material needs time to be uniformly coated all over the entire surface thereof with a solvent, the surface of the porous material may be sufficiently moistened in advance with the same solvent as a solvent in which the silane coupling agent is dissolved. In this case, it is preferred to mix the silane coupling agent to the solvent or to contact for an appropriate amount of time from the time point of replacing with a silane coupling solution.

Hydrolysis of a silane coupling agent may be carried out in advance before the silane coupling agent is brought into contact with a porous material. The hydrolysis and binding may continually proceed at the same time during the contacting step. A method wherein the hydrolysis and binding may continually proceed at the same time during the contacting step is more preferred. This simultaneously progressed treatment can be easily achieved simply by dissolving the silane coupling agent before the hydrolysis in a solvent and bringing the resulting solution into contact to the porous material.

Further, water for hydrolysis may be added to a solution of silane coupling agent. Yet, it is often the case that water adsorbed to the porous material or water infiltrated from the air is sufficient. Therefore, in order to increase efficiency of the subsequent dehydration condensation reaction, it is preferred that water be not added. Further, it is preferred that as much water dissolving in a solvent as possible be removed.

In the porous material after the contacting treatment, an acid anhydride functional group derived from a silane coupling agent is provided. This porous material after the contacting treatment may be subjected to high temperature treatment (baking), for example, at about 100° C. to 300° C., before a hydrolysis treatment.

The binding of a physiologically active substance may be carried out by a method wherein an acid anhydride functional group is once hydrolyzed to a carboxyl group and then the physiologically active substance is brought into contact to the carboxyl group which has been further activated, whereby immobilizing the physiologically active substance. Yet, from the viewpoint of suppressing non-specific adsorption, it is preferred that, without carrying out baking and the treatment for activating or the like of the surface of a porous material, the physiologically active substance be directly brought into contact to an acid anhydride functional group on the surface of the porous material and then immobilized. By this, since the number of steps and time before and after the activation can be decreased, changes of a chemical state (such as adsorption) by a disturbance factor can be suppressed. Therefore, non-specific adsorption can be significantly suppressed.

The term "treatment for activating" herein refers to a treatment wherein an activator is allowed to react with a carboxyl group derived from an acid anhydride functional group on the surface of a solid phase carrier (herein, a porous material) after a treatment for contacting, thereby rendering an activated state. Examples of the activator used herein include carbodiimide and derivatives thereof. Specific examples thereof include 1-ethyl-3-(3-dimethylaminopropyl)carbodiimide (EDC), 1-ethyl-3-(3-dimethylaminopropyl)carbodiimide (EDC) hydrochloride, N,N'-dicyclohexylcarbodiimide (DCC) and N,N'-diisopropylcarbodiimide (DIC). Further, in order to improve reactivity and reaction stability, succinimide or the like can be used in combination therewith. Specific examples thereof include N-hydroxysuccinimide (NHS), N-hydroxysulfosuccinimide (Sulfo-NHS), 3,4-dihydro-3-hydroxy-4-oxo-1,2,3-benzotriazine (Dhbt) and the like.

In a treatment for binding wherein a physiologically active substance is bound to a porous material, such a physiologically active substance is used as a solution thereof dissolved in an appropriate solvent (hereinafter, referred to as a physiologically active substance-containing solution). As the solvent which can be used here, a common solution used as a solvent of the physiologically active substance can be used as is. Examples thereof include water, saline, acetate buffer, citrate buffer, phosphate buffer, HEPES buffer (4-(2-hydroxyethyl)-1-piperazineethanesulfonic acid), MES buffer (2-(N-morpholino)ethanesulfonic acid) and the like. In the treatment for binding, since an acid anhydride functional group or a functional group thereof which is hydrolyzed•activated has in general a high reactivity with a nucleophilic functional group, buffers containing amines such as Tris buffer (trihydroxymethylaminomethane) are not preferred.

In a process of binding wherein a physiologically active substance is bound to a porous material, the binding may carried out by means of a substance which binds•adsorbs with the physiologically active substance. Specific examples includes a method wherein a nitrilotriacetic acid derivative (NTA) and an iminodiacetic acid derivative (IDA) is bound to the acid anhydride-modified surface and a protein having a peptide tag containing plural histidine residues is immobilized thereto.

In cases where a physiologically active substance has a charge opposite to that of the surface of the porous material, it is concentrated on the surface of the porous material and efficiency of binding thereof increases. Since an acid anhydride functional group has a carboxyl group when a part thereof is decomposed, it is therefore thought that the surface thereof is negatively-charged in the case of contacting a solution of a pH of not less than about 3. Because of this, in cases where the pH of the solution is lower than the isoelectric point of the physiologically active substance and not less than 3, the physiologically active substance is positively-charged in the solution and the physiologically active substance has the charge opposite to that of the surface of the porous material. Thus, the efficiency of binding thereof is enhanced. It is therefore preferred, from the point of view that the amount of binding can be increased, that the pH of the solution be not less than 3 and less than the isoelectric point of the physiologically active substance.

After the treatment for binding, from the viewpoint of suppressing non-specific adsorption, it is preferred to carry out a hydrolysis treatment. Since, by this hydrolysis treatment, an unreacted acid anhydride functional group is converted to a carboxyl group, non-specific adsorption is effectively suppressed.

The hydrolysis treatment can be carried out by a conventional known method wherein an acid anhydride functional group is decomposed to generate a carboxyl group. It is generally carried out using an aqueous solution of 20° C. to 100° C. In order to thoroughly complete the hydrolysis reaction, it is preferred that an alkaline or acidic aqueous solution be used. In particular, it is more preferred that an alkaline aqueous solution of a pH of not less than 10 be used. Specific examples thereof include a 1 mM to 1 M aqueous NaOH solution, an aqueous KOH solution and the like. In this case, due to high reactivity, a treatment within 10 minutes is sufficient.

Yet, from the viewpoint of maintaining activity of the bound physiologically active substance, a mild aqueous solution of a pH of 5 to 9 is preferably used. Specific examples thereof include pure water, borate buffer, citrate buffer, phosphate buffer, HEPES buffer, acetate buffer and the like. Furthermore, for the viewpoint of easy operation, a method of holding in a vapor atmosphere can also be exemplified. In the case of these mild methods, it is preferred to treat for not less than 10 minutes. By this, two carboxyl groups are produced from the acid anhydride functional group. As an index for progress of the hydrolysis treatment, a method for measuring a contact angle to water of the porous material or the like after the process can be exemplified.

In a method for producing the carrier of the present invention, a blocking step using a blocking agent is carried out after a step of treating a porous material with a silane coupling agent. In this blocking step, the blocking agent is immobilized to the porous material. The blocking step may be carried out after the treatment with the silane coupling agent. Specifically, for example, it may be carried out immediately after the immobilization of a physiologically active substance, after a hydrolysis treatment, or the same time as the immobilization of the physiologically active substance. In addition, it is possible to simultaneously carry out the hydrolysis treatment by carrying out the immobilization of the blocking agent after the immobilization of the physiologically active substance.

The treatment for blocking may be attained by bringing a blocking agent into contact with a porous material. Although time for the treatment for blocking varies depending on the type and concentration of the blocking agent, the type of the porous material and the like, it is generally preferred, from the viewpoint of carrying out sufficient reaction, that the treatment for blocking be carried out for 0.5 minutes to 120 minutes, more preferably for one minute to 30 minutes. In addition, although the treatment for blocking is generally carried out at 0° C. to 60° C., and from the viewpoint of the stability of a physiologically active substance, at a temperature of 3° C. to 30° C., it may usually be carried out at room temperature (about 25° C.).

Although the concentration of a blocking agent varies depending on the type of the blocking agent, the blocking agent can be generally used at a concentration of 0.1% by mass to 10% by mass, and, from the viewpoint of efficiency, preferably a concentration of 0.3% by mass to 3% by mass. As a solvent in this case, a water-soluble solvent which is usually used for this application can be used as is. Examples thereof include solvents used for the treatment for binding of a physiologically active substance such as water, saline, acetate buffer, citrate buffer, phosphate buffer, HEPES buffer (4-(2-hydroxyethyl)-1-piperazineethanesulfonic acid) or MES buffer (2-(N-morpholino)ethanesulfonic acid), similarly to the solvents used for the treatment for binding of a physiologically active substance.

The thus obtained carrier has a surface onto which a sufficient amount of a physiologically active substance can be immobilized. The amount of the physiologically active substance immobilized to the surface of the carrier can be checked by a method usually used for this purpose. Examples thereof include a method for measuring fluorescence using a fluorescent substance and an RI method using a radioactive isotope.

Since the carrier of the present invention has a blocking agent on the surface thereof, the amount of non-specific adsorption may be sufficiently decreased, and also, the amount of specific binding by a physiologically active substance immobilized to the surface thereof can be satisfactory. As a result, the physiologically active substance is immobilized to the surface at a high density, which allows the ratio (S/N ratio) of a specific binding signal (S) to background by suppression of the amount of non-specific adsorption (N) to be sufficiently large.

Hence, the carrier of the present invention is useful for detection and analysis of molecules specific to the physiologically active substance on the carrier. In particular, it is suitable for a variety of microarrays, biosensors or the like, which require high specificity for the physiologically active substance, such as analysis of a trace amount, or detection of minute interaction.

Also, since the carrier of the present invention includes a porous material having a three-dimensional structure, it is particularly advantageous as a porous material for immunochromatography, which is used for detecting specific adsorption while spreading a sample solution or the like in one direction or in multi-directions, or the like.

3. Acid Anhydride Functional Group-Containing Silane Coupling Agent

An acid anhydride functional group-containing silane coupling agent in the present invention is a silane coupling agent represented by the following Formula (I).

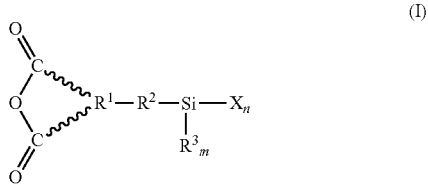

In Formula (I), $R^1$ represents a trivalent linear or branched aliphatic group or aromatic group and, from the viewpoint of stability of the acid anhydride functional group, $R^1$ is preferably any of the followings.

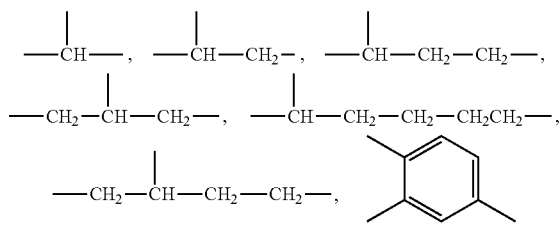

Also, among them, from balance between the stability and reactivity, the following structure is more preferred.

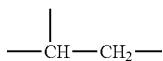

$R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group and, from the viewpoint of efficiency of reaction and suppression of non-specific adsorption after the reaction, $R^2$ is preferably a $C_1$ to $C_5$ linear alkylene group, and more preferably a propylene group.

$R^3$ represents a $C_1$ to $C_{10}$ alkyl group and, from the viewpoint of suppression of non-specific adsorption, $R^3$ is preferably a $C_1$ to $C_2$ alkyl group, and more preferably a methyl group.

X represents a functional group which becomes a hydroxy group by hydrolysis and X is an alkoxy group (—$OR^4$), a halogen atom, or an acyloxy group (—$OOCR^5$), wherein $R^4$ and $R^5$ each independently represent a hydrogen atom or a $C_1$ to $C_{10}$ alkyl group. From the viewpoint of balance between stability and reactivity of X, X is preferably a methoxy group, an ethoxy group, an isopropoxy group, a butoxy group or chlorine, more preferably a methoxy group or an ethoxy group.

n represents 1, 2 or 3, and m represents an integer of (3-n). From the viewpoint of suppression of non-specific adsorption after the reaction, it is preferable that n represents 3 and m represents 0.

Examples of such a silane coupling agent include 3-(triethoxysilyl)propyl succinic acid anhydride, 4-(triethoxysilyl) butyl succinic acid anhydride, 3-(trimethoxysilyl)propyl succinic acid anhydride, 3-(triethoxysilyl)propyl glutaric acid anhydride and the like. From the viewpoint of reactivity and suppression of non-specific adsorption after the reaction, it is preferred to be 3-(triethoxysilyl)propyl succinic acid anhydride.

4. Physiologically Active Substance

In the present invention, a physiologically active substance is not particularly restricted and examples thereof include substances originated from a living body such as proteins, peptides, nucleic acids, sugar chains, lipids, hormones, cytokines, cells or microorganisms, complexes or derivatives thereof, artificial synthetic substances thereof and the like. The physiologically active substance may be a low molecular weight organic compound which is mainly synthesized in vitro such as a vitamin, drug or environmental hormone.

Examples of the proteins include antibodies, antibody-binding proteins, enzymes, sugar chain-recognizing proteins, receptors and the like. The protein may be a purified product of a naturally occurring protein, artificially synthesized one, one in which artificial mutation is introduced, one forming a complex or fragmented one.

As the antibody, various immunoglobulins, that is, IgG, IgM, IgA, IgE and IgD; or a derivative, complex or fragment thereof can be used. Specifically, in cases where a solid phase carrier or porous material is used as a carrier for immunoassay, an antibody against a substance to be measured can be used. Also, as the antibody binding protein, protein G, protein A, protein L or the like can be used and the antibody against a substance to be measured can be immobilized therethrough.

As the enzyme, for example, oxidoreductase, hydrolases, isomerase, lyase, synthetase or the like can be used. The enzyme such as glucose oxidase, cholesterol oxidase, acetylcholinesterase, catecholamines esterase, noradrenaline esterase or dopamine esterase can be used.

Examples of the sugar chain-recognizing proteins include lectins such as ConA or WGA. Examples of the receptors include GPCR (G-proein-coupled receptor), EGFR (Epidermal Growth Factor Receptor) and the like.

As the peptide, naturally occurring one or artificially synthesized one may be used. Further, a peptide into which a non-naturally occurring amino acid is introduced may be used.

As the nucleic acid, DNA, RNA, PNA (peptide nucleic acid) with an arbitrary sequence or a complex thereof can be used. One extracted from nature, ones synthesized by a genetic engineering method or one synthesized chemically may be used. As the sugar chain, oligosaccharide with an arbitrary sequence, polysaccharide or monosaccharide can be used. The length or sequence thereof is controlled may be used and the length or sequence thereof is not strictly controlled may be used as well. An amino group, acetyl amide group, sulfonic acid, or carboxyl group derivative can be used. Further, a glycoprotein in which the sugar chain is bound to a protein can be used. As the lipid, glycerides or complex lipids can be used. The hormone or cytokine may be one produced actually in nature. A synthetic product or derivative thereof can be used. As the cells or microorganisms, ones extracted from nature, subculture thereof or pseudo cells using liposomes may be used.

As the low molecular weight organic compound which is mainly synthesized outside a living body, such as vitamins, drugs or environmental hormones, one whose effects to a living body are unknown or one whose mechanisms of pharmacological actions have been already clarified may be used. Also, one extracted from nature or one synthesized chemically or biochemically may be used.

The disclosures of Japanese Patent Application No. 2008-076724 and Japanese Patent Application No. 2008-076725 are herein incorporated in the present description by reference in their entireties.

All publications, patent applications and technical specifications cited in the present description are herein incorporated into the present description by reference to the same extent as if each individual publication, patent application and technical specification were specifically and individually indicated to be incorporated by reference.

The present invention will now be further specifically described by way of the example thereof. Yet, the scope of the present invention is not limited thereto.

EXAMPLES

1. Immobilization Method, Physiologically Active Substance-Immobilized Carrier and Carrier for Immobilization Example 1

(1) Preparation of Succinic Anhydride-Modified Glass Substrate

In a solution of 2 mol/l 3-(triethoxysilyl)propyl succinic anhydride (manufactured by Gelest) as a silane coupling agent in dry xylene, a washed glass substrate (colorless glass plate manufactured by Matsunami Glass Ind., Ltd.) was immersed, and the reaction was allowed to proceed for 1 hour at room temperature. The reacted glass substrate was removed from the solution in xylene and subjected to 3 times of immersion washing with dry xylene, followed by being dried with nitrogen gas. This glass substrate is hereinafter referred to as succinic anhydride-modified glass.

(2) Immobilization of Antibody and Measurement of Amount of Immobilization

Onto the succinic anhydride-modified glass, a FITC-labeled antibody (manufactured by SIGMA-ALDRICH; hereinafter referred to as IgG-FITC) in acetate buffer (pH 5.0) prepared such that a concentration of 0.1 mg/ml was attained was added dropwise, and the resultant was allowed to react at room temperature at high humidity in the dark for 1 hour. The antibody solution was removed by suction, and the substrate was subjected to immersion washing sequentially in 0.1 M NaOH, in phosphate buffer (PBS), and in pure water in this order, followed by storing the antibody-immobilized glass substrate in PBS (pH 7.1) for 3 days to confirm stable immobilization. The fluorescence intensity of the antibody-immobilized glass substrate was measured with FLA-8000 (manufactured by Fuji Film) (473 nm excitation/530 nm detection), and the amount of the immobilized antibody was computed using a calibration curve prepared in advance.

(3) Measurement of Amount of Non-Specific Adsorption of Antibody

The succinic anhydride-modified glass was prepared, and the glass substrate was immersed in 10 mM borate buffer (pH 8.5) for 1 hour to allow the reaction to proceed (this treatment is hereinafter referred to as the hydrolysis treatment of an acid anhydride). To confirm sufficient progress of the hydrolysis, the static contact angle against water was measured, and it was revealed that the static contact angle had been 36.7±1.1° before the treatment with borate buffer, but it became 7.4±1.1° after the treatment with borate buffer, suggesting production of the carboxyl group due to the hydrolysis. After the reaction, the substrate was washed with running pure water, and an antibody (IgG-FITC) in PBS prepared such that a concentration of 100 nM (15 μg/ml) was attained was added dropwise onto the substrate, followed by leaving the resulting substrate to stand at room temperature at high humidity in the dark for 1 hour. The antibody solution was removed by suction, and the substrate was subjected to immersion washing sequentially in PBS and in pure water in this order. The substrate was then dried in the air, and the amount of non-specific adsorption of the antibody to the substrate was measured using FLA-8000 in the same manner as in the method described above.

Example 2

In the same manner as in Example 1, a succinic anhydride-modified glass was prepared, and the amount of immobilization and the amount of non-specific adsorption of the antibody to the glass were measured. However, the washing with xylene after the reaction with the silane coupling agent was not carried out, and only drying with nitrogen gas was carried out.

Example 3

In the same manner as in Example 1, a succinic anhydride-modified glass was prepared, and the amount of immobilization and the amount of non-specific adsorption of the antibody to the glass were measured. However, the silane coupling agent was prepared as a solution in ethanol, and ethanol was used as the washing liquid.

Example 4

In the same manner as in Example 2, a succinic anhydride-modified glass was prepared, and the amount of immobilization and the amount of non-specific adsorption of the antibody to the glass were measured. However, the silane coupling agent was prepared as a solution in ethanol.

Example 5

In the same manner as in Example 1, a succinic anhydride-modified glass was prepared, and the hydrolysis was carried out by immersion of the glass substrate in 10 mM borate buffer (pH 8.5) at room temperature for 1 hour.

The glass substrate was activated by being brought into contact with DCC•NHS mixed DMF solution (0.1 M each) at room temperature for 1 hour (hereinafter referred to as the activation treatment), followed by 2 times of immersion washing with ethanol and then drying with nitrogen gas. This activated glass substrate was subjected to measurement of the amount of immobilization of the antibody in the same manner as in Example 1.

Further, succinic anhydride-modified glass subjected to the activation treatment in the same manner was immersed in 10 mM HCl for 1 hour at room temperature to completely hydrolyze the activated ester (this operation is hereinafter referred to as the hydrolysis treatment of the activated ester). Using this substrate, the amount of non-specific adsorption of the antibody was measured in the same manner as in Example 1.

Example 6

In the same manner as in Example 5, a succinic anhydride-modified glass was prepared, and the hydrolysis treatment and the activation treatment were carried out, and further, the amount of immobilization and the amount of non-specific adsorption after the hydrolysis treatment, of the antibody to the glass, were measured. However, the silane coupling agent was prepared as a solution in ethanol, and ethanol was used as the washing liquid.

Example 7

In the same manner as in Example 5, a succinic anhydride-modified glass was prepared, and the hydrolysis treatment and the activation treatment were carried out, followed by subjecting the glass to measurement of the amount of immobilization of the antibody and the amount of non-specific adsorption after the hydrolysis treatment. However, instead of the mixed solution of DCC•NHS, an aqueous mixed solution of EDC (manufactured by PIERCE; 0.4 M) and Dhbt (manufactured by Tokyo Chemical Industry Co., Ltd.; 2.8 mM) was used.

Example 8

In the same manner as in Example 1, a succinic anhydride-modified glass was prepared, and the amount of immobilization of the antibody to the glass was measured. However, the silane coupling agent was prepared as a solution in hexane, and hexane was used as the washing liquid.

Comparative Example 1

A succinic anhydride-modified glass was prepared in the same manner as in Example 1, followed by 1 hour of a baking treatment in an oven at 120° C. After allowing the glass to cool to room temperature, the amount of immobilization and the amount of non-specific adsorption of the antibody to the substrate were measured in the same manner as in Example 1.

Comparative Example 2

A succinic anhydride-modified glass was prepared in the same manner as in Example 2, followed by 1 hour of a baking treatment in an oven at 120° C. After allowing the glass to cool to room temperature, the amount of immobilization and the amount of non-specific adsorption of the antibody to the substrate were measured in the same manner as in Example 1.

Comparative Example 3

A succinic anhydride-modified glass was prepared in the same manner as in Example 3, followed by 1 hour of a baking treatment in an oven at 120° C. After allowing the glass to cool to room temperature, the amount of immobilization and the amount of non-specific adsorption of the antibody to the substrate were measured in the same manner as in Example 1.

Comparative Example 4

A succinic anhydride-modified glass was prepared in the same manner as in Example 4, followed by 1 hour of a baking treatment in an oven at 120° C. After allowing the glass to cool to room temperature, the amount of immobilization and the amount of non-specific adsorption of the antibody to the substrate were measured in the same manner as in Example 1.

Comparative Example 5

In the same manner as in Example 5, a succinic anhydride-modified glass was prepared, and the hydrolysis treatment and the activation treatment were carried out, and further, the amount of immobilization and the amount of non-specific adsorption of the antibody to the glass were measured. However, after the reaction with the silane coupling agent, 1 hour of a baking treatment was carried out in an oven at 120° C. before the hydrolysis treatment.

Comparative Example 6

In the same manner as in Example 6, a succinic anhydride-modified glass was prepared, and the hydrolysis treatment and the activation treatment were carried out, and further, the amount of immobilization and the amount of non-specific adsorption of the antibody to the glass were measured. However, after the reaction with the silane coupling agent, 1 hour of a baking treatment was carried out in an oven at 120° C. before the hydrolysis treatment.

Comparative Example 7

A succinic anhydride-modified glass was prepared in the same manner as in Example 1, followed by 1 hour of a baking treatment in an oven at 70° C. After allowing the substrate to cool to room temperature, the amount of immobilization and the amount of non-specific adsorption of the antibody to the substrate were measured.

Comparative Example 8

Onto an aldehyde-modified glass substrate (manufactured by Genetix), FITC-labeled antibody in PBS prepared such that a concentration of 0.1 mg/ml was attained was added dropwise, and the resultant was allowed to react in a high humidity environment for 1 hour. The antibody solution was removed by suction, and the substrate was subjected to immersion washing sequentially in 0.1 M NaOH, in phosphate buffer (PBS), and in pure water in this order, followed by being stored in PBS for 3 days. The amount of immobilization and the amount of non-specific adsorption of the antibody were computed using FLA-8000.

A blocking treatment was carried out on another aldehyde-modified glass substrate by immersion in 2% BSA (bovine serum albumin; manufactured by SIGMA-ALDRICH) solution in PBS to allow the reaction to proceed for 1 hour. The substrate was subjected to immersion washing with PBS and dried in the air. Using this substrate, the amount of non-specific adsorption of the antibody to the substrate was measured in the same manner as in Example 1.

Test Example 1

The above Examples 1 to 8 and Comparative Examples 1 to 8 were compared for the amount of immobilization and the amount of non-specific adsorption of the antibody, and the amount of immobilization/the amount of non-specific adsorption of the antibody. The results are shown in Table 1.

As shown in Table 1, in Examples 1 to 8, carriers showing large amounts of immobilization and large ratios of the amount of immobilization/the amount of non-specific adsorption (exceeding 100) can be obtained.

Further, it was revealed that a larger amount of immobilization and a higher ratio of the amount of immobilization/the amount of non-specific adsorption can be realized by directly binding the antibody without carrying out the activation treatment (Examples 1 to 4).

Further, it was revealed that usage of a nonpolar solvent as the immobilization solvent is more efficient (Examples 1, 2 and 8).

In terms of the washing after the silane coupling reaction, it was revealed that a larger amount of immobilization of the antibody can be obtained in cases where the washing is not carried out (Examples 2 and 4).

TABLE 1

| | Solvent | Washing liquid | Hydrolysis treatment | Activation treatment | Baking | Amount of immobilization of antibody (A) (pg/mm²) | Amount of non-specific adsorption (B) (pg/mm²) | (A)/(B) ratio |
|---|---|---|---|---|---|---|---|---|
| Example 1 | Xylene | Xylene | Borate buffer pH 8.5 | — | None | 2415 | 1.2 | 2013 |
| Example 2 | Xylene | None | ↑ | — | None | 2552 | 1.8 | 1418 |
| Example 3 | Ethanol | Ethanol | ↑ | — | None | 371 | 3.5 | 106 |
| Example 4 | Ethanol | None | ↑ | — | None | 1799 | 1.9 | 947 |
| Example 5 | Xylene | Xylene | ↑ | DCC•NHS | None | 557 | 2.8 | 199 |
| Example 6 | Ethanol | Ethanol | ↑ | ↑ | None | 538 | 5.4 | 101 |
| Example 7 | Xylene | Xylene | ↑ | EDC•Dhbt | None | 1927 | 8.3 | 232 |
| Example 8 | Hexane | Hexane | ↑ | — | None | 2350 | — | — |
| Comparative Example 1 | Xylene | Xylene | Borate buffer pH 8.5 | — | 120° C. | 599 | 31.6 | 19 |
| Comparative Example 2 | Xylene | None | ↑ | — | 120° C. | 260 | 21.5 | 12 |
| Comparative Example 3 | Ethanol | Ethanol | ↑ | — | 120° C. | 257 | 39.5 | 7 |
| Comparative Example 4 | Ethanol | None | ↑ | — | 120° C. | 361 | 11.2 | 32 |
| Comparative Example 5 | Xylene | Xylene | ↑ | DCC•NHS | 120° C. | 630 | 18.1 | 35 |
| Comparative Example 6 | Ethanol | Ethanol | ↑ | ↑ | 120° C. | 538 | 12.4 | 43 |
| Comparative Example 7 | Xylene | Xylene | — | — | 70° C. | 888 | 19.0 | 47 |
| Comparative Example 8 | — | — | — | Aldehyde | None | 2800 | 94.3 | 30 |

Example 9

In the same manner as in Example 1, a succinic anhydride-modified glass substrate was prepared. However, the substrate was not immersed in the solution in xylene, and, instead, the solution in xylene was added dropwise onto the substrate, followed by coating of the substrate with the solution using a spin coater at 1000 rpm for 35 seconds and drying at room temperature (25° C.). Further, in the same manner as in Example 1, the amount of immobilization and the amount of non-specific adsorption of the antibody were measured.

Example 10

In the same manner as in Example 9, succinic anhydride-modified glass was prepared, and the amount of immobilization of the antibody to the glass was measured. However, the silane coupling agent was prepared as a solution in ethanol.

Test Example 2

The respective substrates of Examples 2, Example 4, Example 9 and Example 10 were compared for the amount of immobilization of the antibody. The results are shown in Table 2.

As shown in Table 2 for Examples 2, 4, 9 and 10, it was revealed that the method of contact of the coupling agent with the carrier does not largely affect the amount of immobilization irrespective of whether the method is immersion or spin coating, and that a substrate similarly showing a large amount of immobilization can be provided by either method.

TABLE 2

| | Solvent | Coupling treatment | Amount of immobilization (pg/mm²) |
|---|---|---|---|
| Example 2 | Xylene | Immersion | 2552 |
| Example 4 | Ethanol | ↑ | 1799 |
| Example 9 | Xylene | Spin coating | 2353 |
| Example 10 | Ethanol | ↑ | 2196 |
| Comparative Example 2 | Xylene | Immersion | 260 |
| Comparative Example 4 | Ethanol | ↑ | 361 |

Example 11

In the same manner as in Example 1, succinic anhydride-modified glass was prepared, and the amount of immobilization of the antibody to the glass was measured. However, as the buffer for immobilization of IgG-FITC, an acetate buffer (pH 6.5) was used. The isoelectric point of the antibody used in the present Example was about 6.5.

Test Example 3

Example 1 and Example 11 were compared for the amount of immobilization and the amount of non-specific adsorption of the antibody, and the amount of immobilization/the amount of non-specific adsorption of the antibody. The results are shown in Table 3.

As shown in Table 3, in each of Example 1 and Example 11, the ratio of the amount of non-specific adsorption with respect to the amount of immobilization was small and hence good, irrespective of pH of the immobilization buffer. Further, it was revealed that, by adjusting pH of the immobilization buffer to less than the isoelectric point of the physiologically active substance, a better amount of immobilization and a better balance of the amount of immobilization/the amount of non-specific adsorption can be achieved.

TABLE 3

| | Immobilization buffer | Amount of immobilization of antibody (A) (pg/mm²) | Amount of non-specific adsorption (pg/mm²) | (A)/(B) ratio |
|---|---|---|---|---|
| Example 1 | Acetate buffer pH 5.0 | 2415 | 1.2 | 2013 |

TABLE 3-continued

| | Immobilization buffer | Amount of immobilization of antibody (A) (pg/mm$^2$) | Amount of non-specific adsorption (pg/mm$^2$) | (A)/(B) ratio |
|---|---|---|---|---|
| Example 11 | Acetate buffer pH 6.5 | 510 | 1.2 | 425 |
| Comparative Example 1 | Acetate buffer pH 5.0 | 599 | 31.6 | 19 |

Example 12

In the same manner as in Example 1, succinic anhydride-modified glass was prepared, and the amount of immobilization of the antibody to the glass was measured. However, the substrate was soaked in PBS for 14 days instead of 3 days.

Test Example 4

Example 1 and Example 12 were compared for the amount of immobilization of the antibody. The results are shown in Table 4.

As shown in Table 4, in each of Examples 1 and 12, a large amount of immobilization was maintained even by extending the time of soaking of the antibody-bound glass substrate in PBS to 14 days, showing that the immobilization capacity was stably high.

Thus, it was shown that the modified surface is stable, and has good immobilization capacity in the immobilization method of the first mode of the present invention even without carrying out, immediately after a reaction with a silane coupling agent, the dehydration treatment under high temperature, that is, the so called baking treatment.

TABLE 4

| | Buffer for stability test | Stability test | Amount of immobilization (pg/m$^2$) |
|---|---|---|---|
| Example 1 | PBS | 3 days | 2415 |
| Example 12 | PBS | 14 days | 2356 |
| Comparative Example 1 | PBS | 3 days | 599 |

Example 13

In the same manner as in Example 1, the amount of non-specific adsorption of the antibody to the succinic anhydride-modified glass was measured. However, a 20 mM citrate buffer (pH 6.3) was used as the reaction solution for the hydrolysis treatment of the acid anhydride.

Example 14

In the same manner as in Example 1, the amount of non-specific adsorption of the antibody to the succinic anhydride-modified glass was measured. However, a 0.1 M NaOH solution was used as the reaction solution for the hydrolysis treatment of the acid anhydride, and the reaction was carried out for 30 seconds.

Example 15

In the same manner as in Example 1, the amount of non-specific adsorption of the antibody to the succinic anhydride-modified glass was measured. However, the hydrolysis treatment of the acid anhydride using a borate buffer was not carried out, and non-specific adsorption of the antibody was measured after leaving the substrate to stand at room temperature for 1 hour.

Test Example 5

Example 1 and Examples 13 to 15 were compared for the amount of non-specific adsorption. The results are shown in Table 5.

As shown in Table 5, in each of Examples 1, 13, 14 and 15, a carrier showing only a small amount of non-specific adsorption could be obtained irrespective of the type of the hydrolysis treatment and whether or not the hydrolysis treatment was carried out, and, in particular, by carrying out a hydrolysis treatment, a carrier showing a smaller amount of non-specific adsorption could be obtained.

TABLE 5

| | Hydrolysis treatment | Amount of non-specific adsorption (pg/mm$^2$) |
|---|---|---|
| Example 1 | Borate buffer pH 8.5 | 1.2 |
| Example 13 | Citrate buffer pH 6.3 | 1.7 |
| Example 14 | 0.1 M NaOH (30 seconds) | 0.7 |
| Example 15 | — | 7.8 |
| Comparative Example 1 | Borate buffer pH 8.5 | 31.6 |

Example 16

In the same manner as in Example 1, the amount of non-specific adsorption of the antibody to the succinic anhydride-modified glass was measured. However, the reaction with the silane coupling agent was carried out for 18 hours instead of 1 hour. After the reaction, the succinic anhydride-modified glass was subjected to a hydrolysis treatment of the acid anhydride with a borate buffer or 0.1 M NaOH, resulting in a static contact angle against water of 45.1° or 22.9°, respectively. By this, it was suggested that the surface modification was rather poor compared to the case of Example 1.

Test Example 6

Example 1 and Example 16 were compared for the amount of non-specific adsorption of the antibody. The results are shown in Table 6.

As shown in Table 6, in each of Examples 1 and 16, a carrier showing only a small amount of non-specific adsorption could be obtained irrespective of the length of time of the immobilization, and it was revealed that, in particular, by setting the length of time of the contact of the silane coupling agent with the solid carrier to less than 3 hours, non-specific adsorption can be effectively reduced.

TABLE 6

| | Reaction solvent | Reaction time | Amount of non-specific adsorption (pg/mm$^2$) |
|---|---|---|---|
| Example 1 | Xylene | 1 hour | 1.2 |
| Example 16 | Xylene | 18 hours | 4.5 |

Example 17

Figure 1B:
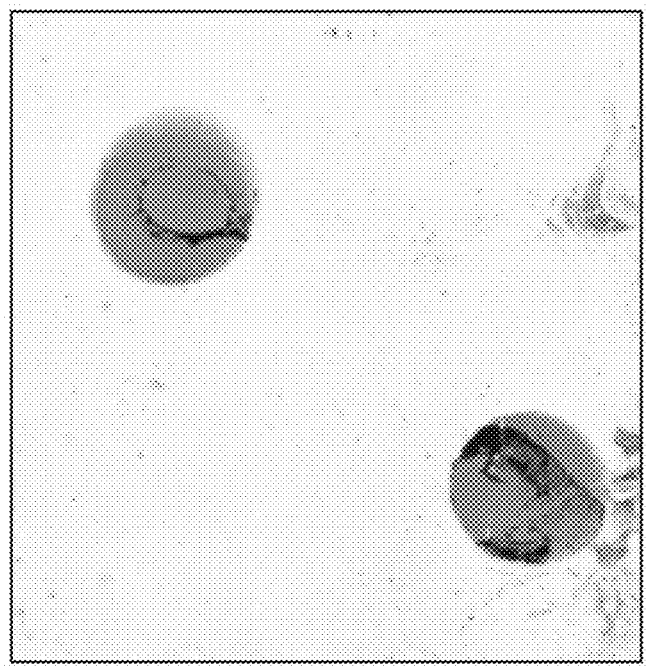
FIG. 1B shows a fluorograph of the physiologically active substance-immobilized carrier (antigen concentration: 100 nM) of Example 17.

In the same manner as in Example 1, succinic anhydride-modified glass was prepared, and the antibody was immobilized thereto. However, as the antibody, an anti-CRP monoclonal antibody (manufactured by Fitzgerald) was used. A 1 nM Cy5 (manufactured by GE Healthcare Biosciences)-labeled CRP antigen (manufactured by Oriental Yeast Co., Ltd.) in PBS and a 100 nM Cy5 (manufactured by GE Healthcare Biosciences)-labeled CRP antigen (manufactured by Oriental Yeast Co., Ltd.) in PBS were prepared respectively, and the resulting solution was applied to the entire surface of the substrate on which the antibody had been immobilized. The substrate was then left to stand at room temperature at high humidity in the dark for 1 hour to allow antigen-antibody reaction to proceed. Thereafter, the substrate was subjected to immersion washing sequentially in PBS and in pure water in this order. The amount of immobilization to the antibody immobilization area and the amount of non-specific adsorption of the antibody to the antibody non-immobilization area were measured using FLA-8000 (635 nm excitation/675 nm detection), and the ratio between these (the amount of specific binding/the amount of non-specific adsorption: S/N ratio) was calculated. The results are shown in Table 7 and FIGS. 1A and 1B.

Comparative Example 9

Figure 2A:
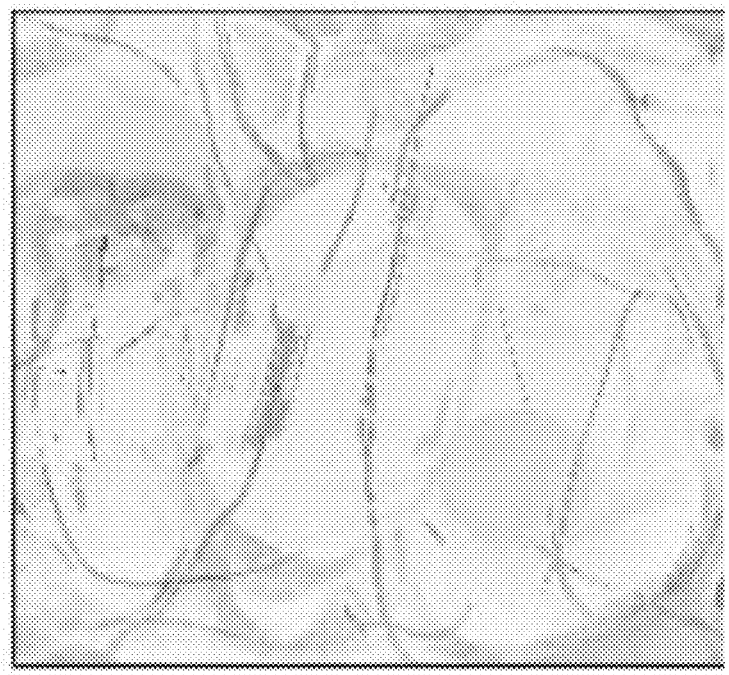
FIG. 2A shows a fluorograph of the physiologically active substance-immobilized carrier (antigen concentration: 1 nM) of Comparative Example 9.
Figure 2B:
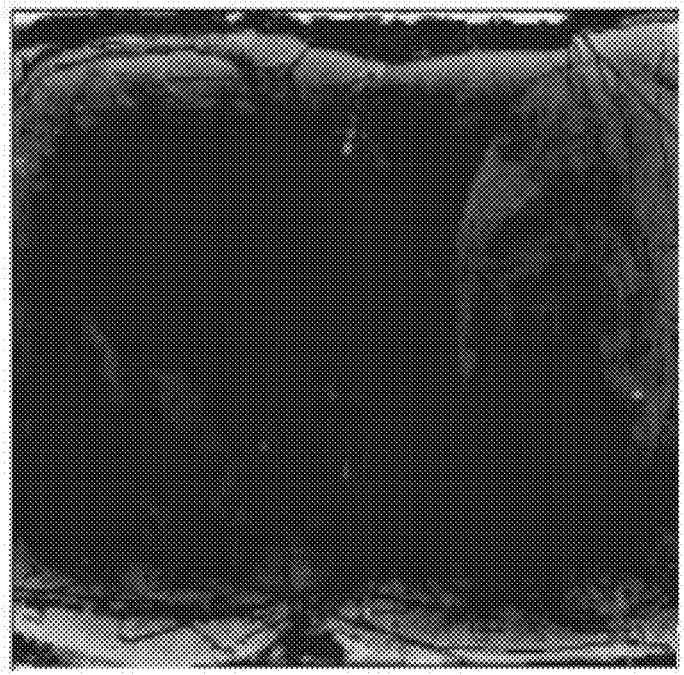
FIG. 2B shows a fluorograph of the physiologically active substance-immobilized carrier (antigen concentration: 100 nM) of Comparative Example 9.

In the same manner as in Comparative Example 8, the anti-CRP antibody was immobilized on the aldehyde-modified glass, and the blocking treatment was carried out in the same manner as in Comparative Example 8 over the entire surface of the substrate including the antibody immobilization area. In the same manner as in Example 17, the amount of binding and the amount of non-specific adsorption of the Cy5-modified CRP were measured to calculate the S/N ratio. The results are shown in Table 7 and FIGS. 2A and 2B.

Example 18

The anti-CRP-antibody was immobilized in the same manner as in Example 17. After washing, a FITC-labeled CRP antibody, the CRP antibody (manufactured by Fitzgerald; hereinafter referred to as the secondary antibody) of which is different from the antibody immobilized on the substrate and can form a sandwich, was prepared in PBS supplemented with 1% BSA such that a concentration of 100 nM (15 µg/ml) was attained, and the prepared solution was mixed with CRP antigen (non-labeled) solutions (in PBS supplemented with 1% BSA) of various concentrations. After being left to stand for 1 hour, each mixed solution was applied to the entire surface of the antibody-immobilized substrate. Thereafter, the substrate was left to stand at room temperature at high humidity in the dark for 1 hour to allow antigen-antibody reaction to proceed. Immersion washing was then carried out sequentially in PBS and pure water. The amount of binding of the secondary antibody to the antibody immobilization area was measured (473 nm excitation/530 nm detection), and the ratio between the amount observed under each antigen concentration condition and the amount observed under the condition where the antigen was not included (the amount of specific binding/the amount of non-specific adsorption: S/N ratio) was calculated. The results are shown in Table 7.

As shown in Table 7, the physiologically active substance-immobilized carriers in Examples 17 and 18 showed high S/N ratios irrespective of the antigen concentration, which S/N ratios were not less than one order of magnitude higher than that of aldehyde-modified where the secondary antibody was used, a S/N ratio of 9.5, which is a very good value, was observed even with an antigen concentration of 10 pM.

TABLE 7

| | Surface modification | Antigen concentration | Secondary antibody | S/N ratio |
|---|---|---|---|---|
| Example 17 | Succinic anhydride-modified | 1 nM | — | 26.2 |
| | Succinic anhydride-modified | 100 nM | — | 68.5 |
| Example 18 | Succinic anhydride-modified | 0 M | 100 nM | 1.0 |
| | Succinic anhydride-modified | 10 pM | 100 nM | 9.5 |
| | Succinic anhydride-modified | 100 pM | 100 nM | 21.3 |
| | Succinic anhydride-modified | 1 nM | 100 nM | 189.3 |
| Comparative Example 9 | Aldehyde-modified | 1 nM | — | 2.2 |
| | Aldehyde-modified | 100 nM | — | 1.1 |

Accordingly, according to the first mode of the present invention, a physiologically active substance-immobilized carrier with which non-specific adsorption is suppressed and on which a sufficient amount of the physiologically-active substance is immobilized; and a carrier for immobilization useful therefor; can be obtained.

2. Carrier and Method for Producing It.

Example 1B (1) Preparation of Succinic Anhydride-Modified Glass Membrane

In a solution of 2 mmol/l 3-(triethoxysilyl)propyl succinic anhydride (manufactured by Gelest) as a silane coupling agent in dry xylene, a glass membrane (GF/A manufactured by Whatman; 10 mm×35 mm, 1.6 µm pore size (particle capture)) that had been preliminarily treated with UV/ozone and washed with dry xylene was immersed, and the reaction was allowed to proceed at room temperature with stirring for 1 hour. The reacted glass membrane was subjected to immersion washing twice with dry xylene and then twice with acetone, followed by drying the glass membrane to allow acetone to evaporate. This glass membrane is referred to as a succinic anhydride-modified membrane (this may also be simply referred to as "membrane").

(2) Blocking of Succinic Anhydride-Modified Membrane

The succinic anhydride-modified membrane prepared in (1) above was immersed sequentially in 100 mM aqueous NaOH solution, in PBS (phosphate buffer) and in pure water in this order for 30 seconds each. The succinic anhydride-modified membrane was taken out and water was partially removed therefrom, followed by impregnating the membrane with 150 µl of the blocking solution below or pure water.

1% BSA solution (bovine serum albumin; manufactured by Sigma-Aldrich) in PBS

N-102 (a blocking agent manufactured by Nippon Oil & Fats Co., Ltd; used without dilution)

NanoBioBlocker (a blocking agent manufactured by Nanobiotech; used without dilution)

The blocking treatment was carried out by leaving the membrane to stand at room temperature for 1 hour, followed by 30 seconds each of immersion washing with PBS and then with pure water. N-102 is a synthetic compound based blocking agent and thought to have a water-soluble polymer that suppresses non-specific adsorption, and an adsorptive group.

NanoBioBlocker is thought to be a compound in which polyethylene glycol and an oligoamine are bound.

(3) Preparation of Succinic Anhydride-Modified Glass Slide

In the same manner as in the case of the succinic anhydride-modified membrane, the reaction with the silane coupling agent and washing were carried out for a glass slide (white edge, polished; manufactured by Matsunami Glass Ind., Ltd.). This glass slide is referred to as a succinic anhydride-modified slide (this may also be simply referred to as "slide"). Further, in the same manner as in the case of the membrane, a blocking treatment was carried out.

(4) Analysis of Amount of Non-Specific Adsorption

The above blocked succinic anhydride-modified membrane and succinic anhydride-modified slide were impregnated with 150 μl of 10 nM Cy5-modified CRP (prepared by labeling CRP manufactured by Oriental Yeast Co., Ltd. with Cy5 manufactured by GE Healthcare Biosciences), or 150 μl of the Cy5-modified CRP solution was added onto the membrane and the slide dropwise. The membrane and the slide were left to stand at room temperature at high humidity in the dark for 1 hour. These were subjected to immersion washing twice with PBS and then twice with pure water, followed by measurement of the fluorescence intensity with FLA-8000 (manufactured by Fuji Film) (635 nm excitation/675 nm detection). The fluorescence intensity (amount of non-specific adsorption) of each of the blocked membrane and slide was calculated as the ratio with respect to that obtained using pure water instead of carrying out the blocking treatment. That is, a value higher than 1 indicates that the amount of non-specific adsorption increased by the blocking treatment, while a smaller value indicates a higher level of suppression of non-specific adsorption by the blocking treatment. The results are shown in Table 8.

As shown in Table 8, with the succinic anhydride-modified membranes, the ratios of the amounts of non-specific adsorption were not more than 1 irrespective of the type of the blocking agent, ranging from 0.02 to 0.17. This means that, in the carriers using a porous material, the amount of non-specific adsorption was decreased by the blocking treatment. On the other hand, in the succinic anhydride-modified slides, the ratios of the values obtained in the cases where the blocking treatment was carried out relative to the value obtained in the case where the blocking treatment was not carried out were 1.02 to 3.5, indicating that the effect of the blocking agent was not sufficiently exerted and hence that the amount of non-specific adsorption increased. Therefore, it was shown that the nonspecific-adsorption-suppression effect of the blocking agent, which was ineffective or adversely effective on the surface of a nonporous material, is effective in a porous material.

TABLE 8

| | Ratio of amount of non-specific adsorption | |
|---|---|---|
| | Slide | Membrane |
| BSA | 1.18 | 0.02 |
| N-102 | 1.02 | 0.02 |
| NanoBio | 3.46 | 0.17 |

Example 2B

Onto a succinic anhydride-modified membrane prepared in the same manner as in Example 1B, 3 μl of a 0.1 mg/ml anti-CRP monoclonal antibody (manufactured by Fitzgerald; #701289) in 10 mM acetate buffer (pH 5.0) was added dropwise, followed by allowing the reaction to proceed at room temperature at high humidity in the dark for 1 hour. Immersion washing was carried out sequentially with 0.1 M NaOH, with phosphate buffer (PBS) and with pure water in this order, and the membrane was impregnated with 150 μl of the blocking solution below or pure water.

1% BSA, pH 5 (solution in PBS)
1% BSA, pH 7 (solution in acetate buffer)
1% casein (solution in TBS: manufactured by PIERCE)
N-102 (a blocking agent manufactured by Nippon Oil & Fats Co., Ltd; used without dilution)
NanoBioBlocker (a blocking agent manufactured by Nanobiotech; used without dilution)

The blocking treatment was carried out by leaving each membrane to stand at room temperature for 1 hour, followed by 30 seconds each of immersion washing with PBS and then with pure water.

Each succinic anhydride-modified membrane after the antibody immobilization treatment and the blocking treatment was impregnated with 150 μl of Cy5-modified CRP (10 nM solution in PBS). The membrane was then left to stand at room temperature at high humidity in the dark for 1 hour. Thereafter, the membrane was subjected to immersion washing twice with PBS and then twice with pure water, followed by measurement of the fluorescence intensity with FLA-8000 (635 nm excitation/675 nm detection). The amount of binding of CRP to the area on which the anti-CRP antibody was immobilized (signal value: S) and the amount of non-specific adsorption of CRP to the area on which the anti-CRP antibody was not immobilized (noise: N) were measured. Further, the ratio between these (S/N ratio) was calculated. The results are shown in Table 9. The fluorescent images obtained in the case where blocking was not carried out and in the case where NanoBioBlocker was used are shown in FIGS. 3A and 3B.

As shown in Table 9, the amounts of non-specific adsorption (N) in the samples subjected to the blocking treatment drastically decreased to be one sixth to one fiftieth of that of the sample without the blocking treatment. Further, the amount of binding (S) was confirmed to have been enhanced by not less than 1.5-fold in all the samples subjected to the blocking treatment, compared to the sample without the blocking treatment. Further, in the case without the blocking, the S/N ratio was about 0.5 and therefore the detection was unsuccessful, while the samples subjected to the blocking treatment showed ratios of 4.4 to 45, indicating that the detection could be sufficiently carried out in these cases.

Figure 3A:
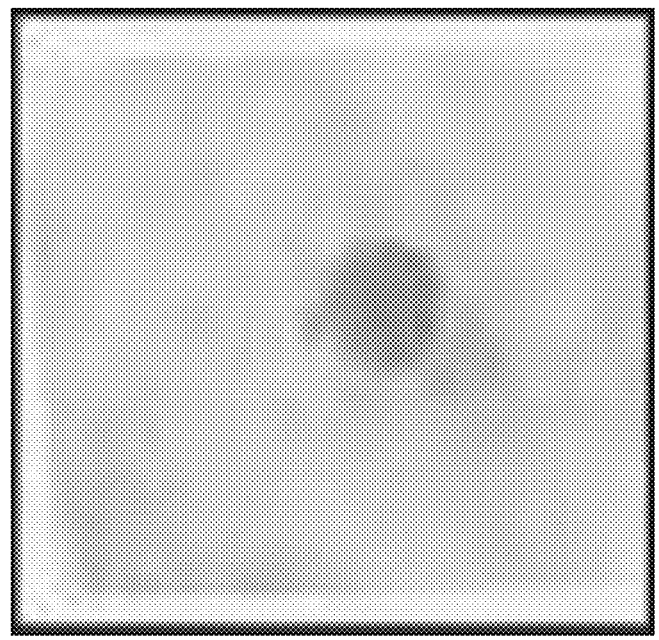
FIG. 3A shows a fluorescent image showing a result of detection of Cy5-labeled CRP on the membrane which was subjected to the blocking treatment of Example 2B.
Figure 3B:
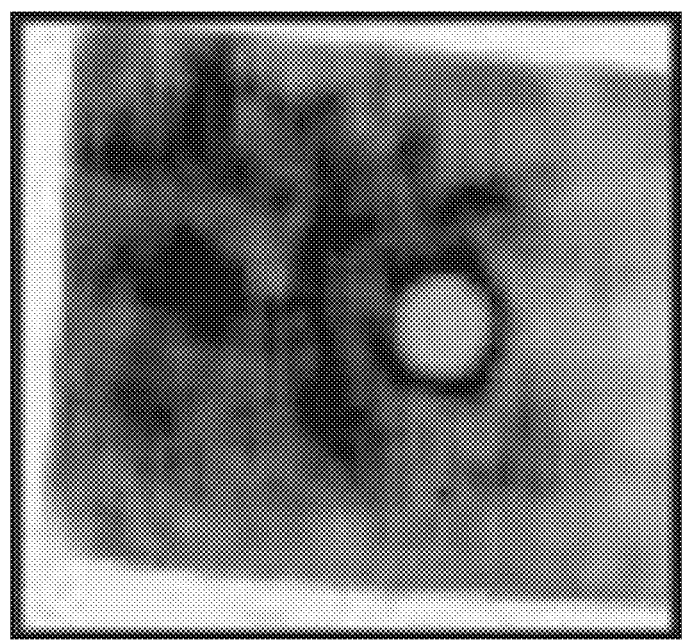
FIG. 3B shows a fluorescent image showing a result of detection of Cy5-labeled CRP on the membrane which was not subjected to the blocking treatment of Example 2B.

Further, in FIGS. 3A and 3B, in the case where the blocking was carried out (FIG. 3A), the fluorescence of the area onto which the Cy5-modified CRP was added dropwise was stronger, while the fluorescence in the vicinity thereof remained weak. As a result, the area where the fluorescence developed can be seen clearly. On the other hand, in the case without the blocking (FIG. 3B), the fluorescence intensity of the area onto which the Cy5-modified CRP was added dropwise was weaker compared to the case where the blocking was carried out, and, moreover, the fluorescence due to non-specific adsorption to the vicinity was strong.

TABLE 9

| | Amount of binding/adsorption (a.u.) | | |
|---|---|---|---|
| | S | N | S/N |
| None | 15130 | 30826 | 0.49 |
| BSA pH 5 | 27866 | 877 | 31.29 |

TABLE 9-continued

| | Amount of binding/adsorption (a.u.) | | |
|---|---|---|---|
| | S | N | S/N |
| BSA pH 7 | 25188 | 585 | 43.03 |
| Casein | 24824 | 2360 | 10.52 |
| N-102 | 28297 | 632 | 44.77 |
| NanoBio | 22986 | 5230 | 4.40 |

Example 3B

In the same manner as in Example 2B, an anti-CRP antibody (manufactured by Fitzgerald; #7111422) was immobilized on the succinic anhydride-modified membrane, and the blocking treatment was carried out. However, the blocking treatment was carried out with NanoBioBlocker or N-102.

Equal volumes of a 100 nM FITC-modified anti-CRP monoclonal antibody (which was obtained by subjecting #701289 manufactured by Fitzgerald to labeling with FITC manufactured by DOJINDO LABORATORIES and to purification) in PBS supplemented with 1% BSA, and CRP prepared such that various concentrations (10 pM to 10 nM) were attained were mixed together, followed by leaving the resulting mixture to stand for 1 hour in advance to allow the reaction to proceed. The membrane after the antibody immobilization and the blocking treatment was impregnated with 200 µl of the mixed solution of the antigen and the antibody, followed by being left to stand at room temperature at high humidity in the dark for 1 hour. The membrane was then subjected to immersion washing twice with PBS and then twice with pure water, followed by measurement of the fluorescence intensity with FLA-8000 (473 nm excitation/530 nm detection). The acceptable limit of noise by FLA-8000 was set to 1000.

The amount of binding of the FITC-modified anti-CRP antibody to the area on which the anti-CRP antibody was immobilized (signal value: S) and the amount of non-specific adsorption to the area on which the anti-CRP antibody was not immobilized (noise: N) were measured. Further, the ratio between these (S/N ratio) was calculated. The results are shown in Table 10.

As shown in Table 10, the amount of non-specific adsorption (N) was not more than the detection limit (1000) under all the conditions. Further, it was shown that the amount of binding (S) increases in an antigen concentration-dependent manner at antigen concentrations of not less than 10 pM in cases where NanoBioBlocker was used and at antigen concentrations of not less than 1 nM in cases where N-102 was used.

TABLE 10

| | Con- | Amount of binding/adsorption (a.u.) | | |
|---|---|---|---|---|
| | centration | S | N | S/N |
| NanoBio | 10 pM | 1038.46 | 856.31 | 1.2 |
| | 100 pM | 1200.81 | 163.88 | 7.3 |
| | 1 nM | 1876.80 | 488.83 | 3.8 |
| | 10 nM | 3991.89 | 151.95 | 26.3 |
| N-102 | 10 pM | 146.79 | 25.35 | 5.8 |
| | 100 pM | −190.08 | −302.86 | 0.6 |
| | 1 nM | 1115.34 | −393.47 | 2.8 |
| | 10 nM | 2518.01 | −521.37 | 4.8 |

Example 4B

In the same manner as in Example 1B, succinic anhydride-modified membrane was prepared, and the membrane was immersed sequentially in 100 mM NaOH solution, in PBS and in pure water in this order. Subsequently, a part of the membrane was dried at 70° C. for 1 hour (baking treatment). The part of the membrane and untreated glass membrane were subjected to the blocking treatment in the same manner as in Example 1B. However, as the blocking agent, NanoBioBlocker was used. Further, in the same manner as in Example 1B, the amount of non-specific adsorption of Cy5-modified CRP was measured. The results are shown in Table 11.

As shown in Table 11, although non-specific adsorption was largely suppressed by the blocking treatment also under the condition with the baking treatment, the adsorption suppression capacity was higher in the case without the baking treatment, so that it was shown that it is more preferable not to conduct the baking treatment.

TABLE 11

| | Blocking treatment | Amount of non-specific adsorption (a.u.) |
|---|---|---|
| No treatment | No | 35829 |
| | Yes | 9469 |
| SA + Baking | No | 25960 |
| | Yes | 4840 |
| SA | No | 5923 |
| | Yes | 2483 |

Example 5B

In the same manner as in Example 2B, an anti-hCG antibody was immobilized on succinic anhydride-modified membrane, followed by the blocking treatment. However, for the blocking treatment, 1% BSA, NanoBioBlocker or pure water (no blocking) was used, respectively. Each membrane after the antibody immobilization and blocking was incorporated into an immunochromatographic kit, and used for development with a 180 pM hCG solution prepared with PBS supplemented with 1% BSA.

Before the development in the antibody-immobilized membrane, the hCG solution was allowed to pass through a glass pad in which anti-hCG antibody-immobilized gold colloid was retained, so that the solution was allowed to develop while suspending the gold colloid.

Since, by this, a sandwich structure is formed among the three members, that is, the antibody immobilized on the membrane, the hCG antigen and the antibody immobilized on the gold colloid, presence/absence of the antigen can be detected based on the amount of the gold colloid remaining on the antibody-immobilized area. This method is referred to as immunochromatography.

Figure 4A:
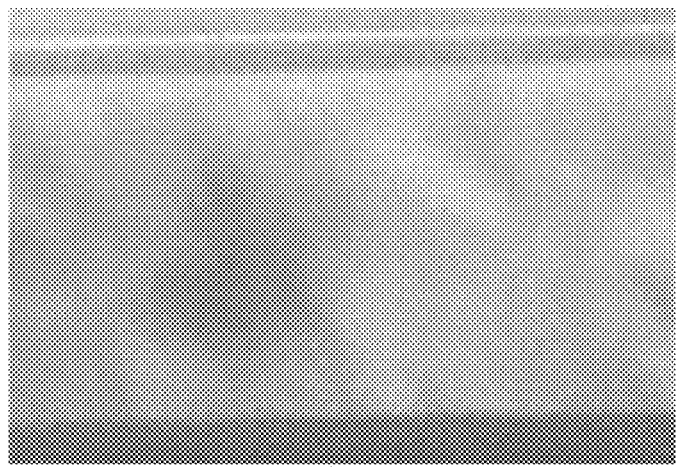
FIG. 4A shows an image showing a result of immunochromatography of the membrane which was subjected to the BSA blocking treatment of Example 5B.
Figure 4B:
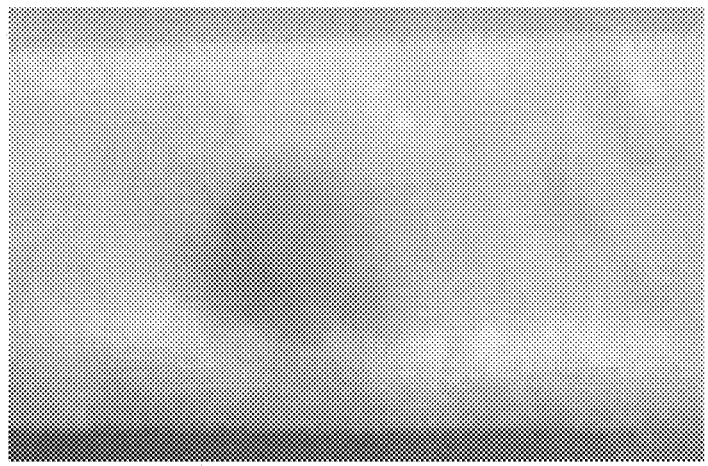
FIG. 4B shows an image showing a result of immunochromatography of the membrane which was subjected to the NanoBioBlocker blocking treatment of Example 5B.
Figure 4C:
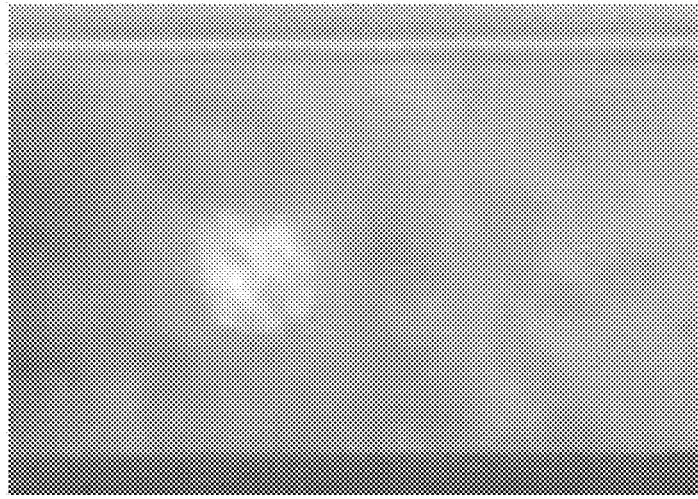
FIG. 4C shows an image showing a result of immunochromatography of the membrane which was not subjected to the blocking treatment of Example 5B.

The amount of gold colloid remaining on the antibody-immobilized area (S) and the amount of gold colloid remaining in the vicinity thereof (N) were quantified by analyzing the brightness of magenta in recorded images, using Photoshop manufactured by Adobe Systems. However, since there is a possibility that the offset value could not be removed from each obtained value, the calculated S/N ratio may be smaller than the actual ratio. The results are shown in Table 12, and the images analyzed are shown in FIGS. 4A, 4B and 4C.

As shown in Table 12, in the case without the blocking treatment, the S/N ratio was 0.62, which is smaller than 1, and as a result, the remaining amount of gold colloid was smaller in the antibody-immobilized area than in the vicinity thereof. On the other hand, the blocking treatment using BSA or NanoBioBlocker resulted in increase in S and suppression of N, leading to a S/N ratio of not less than 1, with which the detection could be carried out advabtageously. Thus, also in the evaluation system by immunochromatography using gold colloid, superiority of the process in which the blocking treatment is carried out was demonstrated.

TABLE 12

|  | Amount of binding/adsorption (a.u.) | | |
| --- | --- | --- | --- |
|  | S | N | S/N |
| 1% BSA | 73.28 | 43.71 | 1.68 |
| NanoBio | 74.67 | 42.08 | 1.77 |
| No blocking | 32.46 | 52.76 | 0.62 |

Embodiments of the present invention are described below, but the present invention is not restricted thereto.

<1> An immobilization method for immobilizing a physiologically active substance on a solid phase carrier, the method comprising:

bringing the solid phase carrier into contact with an acid anhydride functional group-containing silane coupling agent represented by the following Formula (I); and carrying out a treatment for binding of the physiologically active substance to the acid anhydride functional group while maintaining the solid phase carrier after the contact at a temperature within the range of 0° C. to 60° C.

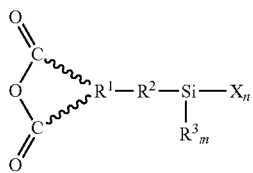

(I)

In Formula (I), $R^1$ represents a trivalent linear or branched aliphatic group or aromatic group; $R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group; $R^3$ represents a hydrogen atom or a $C_1$ to $C_{10}$ alkyl group; X represents an alkoxy group (—$OR^4$), a halogen atom or an acyloxy group (—$OOCR^5$), wherein $R^4$ and $R^5$ each independently represent a hydrogen atom or a $C_1$ to $C_{10}$ alkyl group; n represents 1, 2 or 3; and m represents an integer of (3−n).

<2> The immobilization method according to <1>, wherein in the treatment for binding, the physiologically active substance is directly brought into contact with, and bound to, the acid anhydride functional group.

<3> The immobilization method according to <1> or <2>, comprising carrying out a hydrolysis treatment of the solid phase carrier to which the physiologically active substance is bound.

<4> The immobilization method according to any one of <1> to <3>, wherein a solution of the silane coupling agent in a nonpolar organic solvent is brought into contact with the solid phase carrier.

<5> The immobilization method according to any one of <1> to <4>, wherein the solid phase carrier is not washed after the contact with the silane coupling agent.

<6> The immobilization method according to any one of <1> to <5>, wherein the silane coupling agent is kept in contact with the solid phase carrier for less than 3 hours.

<7> The immobilization method according to any one of <1> to <6>, wherein the treatment for binding is carried out using a physiologically-active-substance solution having a pH of not less than 3 and less than the isoelectric point of the physiologically active substance.

<8> A physiologically-active-substance-immobilized carrier prepared by immobilizing a physiologically active substance on a solid phase carrier by the method according to any one of <1> to <7>.

<9> An carrier for immobilization obtained by bringing the solid phase carrier into contact with an acid anhydride functional group-containing silane coupling agent represented by the following Formula (I), and used for preparing the physiologically-active-substance-immobilized carrier according to <8>.

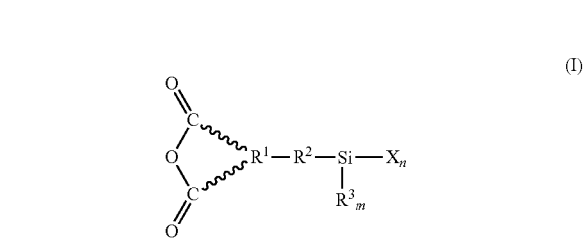

In Formula (I), in Formula (I), $R^1$ represents a trivalent linear or branched aliphatic group or aromatic group; $R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group; $R^3$ represents a hydrogen atom or a $C_1$ to $C_{10}$ alkyl group; X represents an alkoxy group (—$OR^4$), a halogen atom or an acyloxy group (—$OOCR^5$), wherein $R^4$ and $R^5$ each independently represent a hydrogen atom or a $C_1$ to $C_{10}$ alkyl group; n represents 1, 2 or 3; and m represents an integer of (3−n).

<10> A carrier comprising a porous material treated with an acid anhydride functional group-containing silane coupling agent represented by the following Formula (I), and a blocking agent that is immobilized on the porous material.

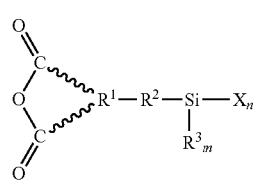

(I)

In Formula (I), in Formula (I), $R^1$ represents a trivalent linear or branched aliphatic group or aromatic group; $R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group; $R^3$ represents a hydrogen atom or a $C_1$ to $C_{10}$ alkyl group; X represents an alkoxy group (—$OR^4$), a halogen atom or an acyloxy group (—$OOCR^5$), wherein $R^4$ and $R^5$ each independently represent a hydrogen atom or a $C_1$ to $C_{10}$ alkyl group; n represents 1, 2 or 3; and m represents an integer of (3−n).

<11> The carrier according to <10>, wherein the blocking agent comprises as a partial structure at least one selected from the group consisting of a water-soluble polymer and a water-soluble protein.

<12> The carrier according to <10> or <11>, wherein the blocking agent comprises at least one selected from the group consisting of albumin, casein, gelatin, polyethylene glycol, a phosphorylcholine group-containing polymer, a polysaccharide, polyvinyl alcohol, polyhydroxyethyl methacrylate, polyacrylic acid, polyacrylamide, a zwitter ion-containing polymer, and polyvinyl pyrrolidone.

<13> The carrier according to any one of <10> to <12>, wherein the surface of the porous material is an inorganic oxide or an inorganic nitride.

<14> The carrier according to any one of <10> to <13>, wherein the porous material has a pore size of 1 nm to 1 mm.

<15> The carrier according to any one of <10> to <14>, wherein a physiologically active substance is bound to the surface of the porous material.

<16> The carrier according to any one of <10> to <15>, which is a carrier for immunochromatography.

<17> A method for producing a carrier, the method comprising:
treating a porous material with an acid anhydride functional group-containing silane coupling agent represented by the following Formula (I); and
bringing the porous material treated with the silane coupling agent into contact with a blocking agent.

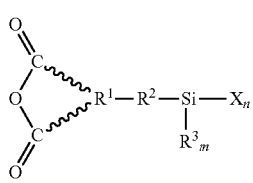

(I)

In Formula (I), in Formula (I), $R^1$ represents a trivalent linear or branched aliphatic group or aromatic group; $R^2$ represents a substituted or unsubstituted $C_1$ to $C_{20}$ alkylene group, a substituted or unsubstituted $C_1$ to $C_{20}$ arylene group, a substituted or unsubstituted $C_1$ to $C_{20}$ arylalkylene group or a substituted or unsubstituted $C_1$ to $C_{20}$ alkylarylene group; $R^3$ represents a hydrogen atom or a $C_1$ to $C_{10}$ alkyl group; X represents an alkoxy group (—$OR^4$), a halogen atom or an acyloxy group (—$OOCR^5$), wherein $R^4$ and $R^5$ each independently represent a hydrogen atom or a $C_1$ to $C_{10}$ alkyl group; n represents 1, 2 or 3; and m represents an integer of (3−n).

<18> The method for producing a carrier according to <17>, further comprising directly bringing the physiologically active substance into contact with, and binding to, the acid anhydride functional group, before the contact of the porous material with the blocking agent.

<19> The method for producing a carrier according to <18>, comprising carrying out a hydrolysis treatment of the carrier to which the physiologically active substance is bound.

<20> The method for producing a carrier according to any one of <17> to <19>, comprising
carrying out a treatment for binding of the physiologically active substance to the acid anhydride functional group while maintaining the carrier after the contact with the silane coupling agent at a temperature within the range of 0° C. to 60° C.

The invention claimed is:

1. A carrier comprising a porous material treated with an acid anhydride functional group-containing silane coupling agent represented by the following Formula (I), and a blocking agent that is immobilized on the porous material:

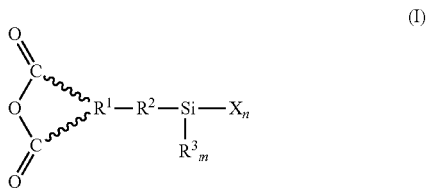

(I)

wherein, in Formula (I), $R^1$ represents a trivalent linear or branched aliphatic group or aromatic group; $R^2$ represents a substituted or unsubstituted $C_1$ to $C_5$ alkylene group; $R^3$ represents a hydrogen atom or a $C_1$ to $C_{10}$ alkyl group; X represents an alkoxy group (—$OR^4$), wherein $R^4$ represents a hydrogen atom or a $C_1$ to $C_{10}$ alkyl group; n represents 3; and m represents 0.

2. The carrier according to claim 1, wherein the blocking agent comprises as a partial structure at least one selected from the group consisting of a water-soluble polymer and a water-soluble protein.

3. The carrier according to claim 1, wherein the blocking agent comprises at least one selected from the group consisting of albumin, casein, gelatin, polyethylene glycol, a phosphorylcholine group-containing polymer, a polysaccharide, polyvinyl alcohol, polyhydroxyethyl methacrylate, polyacrylic acid, polyacrylamide, a zwitter ion-containing polymer, and polyvinyl pyrrolidone.

4. The carrier according to claim 1, wherein the surface of the porous material is an inorganic oxide or an inorganic nitride.

5. The carrier according to claim 1, wherein the porous material has a pore size of 1 nm to 1 mm.

6. The carrier according to claim 1, wherein a physiologically active substance is bound to the surface of the porous material.

7. The carrier according to claim 1, which is a carrier for immunochromatography.

8. A method for producing a carrier, the method comprising:
treating a porous material with an acid anhydride functional group-containing silane coupling agent represented by the following Formula (I); and
bringing the porous material treated with the silane coupling agent into contact with a blocking agent:

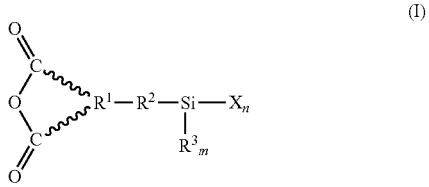

(I)

wherein, in Formula (I), $R^1$ represents a trivalent linear or branched aliphatic group or aromatic group; $R^2$ represents a substituted or unsubstituted $C_1$ to $C_5$ alkylene group; $R^3$ represents a hydrogen atom or a $C_1$ to $C_{10}$ alkyl group; X represents an alkoxy group (—OR), wherein $R^4$ represents a hydrogen atom or a $C_1$ to $C_{10}$ alkyl group; n represents 3; and m represents 0.

9. The method for producing a carrier according to claim 8, further comprising directly bringing the physiologically active substance into contact with, and binding to, the acid anhydride functional group, before the contact of the porous material with the blocking agent.

10. The method for producing a carrier according to claim 9, comprising carrying out a hydrolysis treatment of the carrier to which the physiologically active substance is bound.

11. The method for producing a carrier according to claim 8, comprising carrying out a treatment for binding of the physiologically active substance to the acid anhydride functional group while maintaining the carrier after the contact with the silane coupling agent at a temperature within the range of 0° C. to 60° C.

12. The carrier according to claim 1, wherein the acid anhydride functional group-containing silane coupling agent represented by Formula (I) is selected from the group consisting of 3-(triethoxysilyl)propyl succinic acid anhydride, 4-(triethoxysilyl)butyl succinic acid anhydride, 3-(trimethoxysilyl)propyl succinic acid anhydride and 3-(triethoxysilyl) propyl glutaric acid anhydride.

13. The carrier according to claim 1, wherein the acid anhydride functional group-containing silane coupling agent represented by Formula (I) is 3-(triethoxysilyl)propyl succinic acid anhydride.

14. The method for producing a carrier according to claim 8, wherein the acid anhydride functional group-containing silane coupling agent represented by Formula (I) is selected from the group consisting of 3-(triethoxysilyl)propyl succinic acid anhydride, 4-triethoxysilyl) butyl succinic acid anhydride, 3-(trimethoxysilyl)propyl succinic acid anhydride and 3-(triethoxysilyl)propyl glutaric acid anhydride.

15. The method for producing a carrier according to claim 8, wherein the acid anhydride functional group-containing silane coupling agent represented by Formula (I) is 3-(triethoxysilyl)propyl succinic acid anhydride.

* * * * *